US007691359B2

(12) United States Patent
Tour et al.

(10) Patent No.: US 7,691,359 B2
(45) Date of Patent: Apr. 6, 2010

(54) CARBON NANOTUBES DERIVATIZED WITH DIAZONIUM SPECIES

(75) Inventors: James M. Tour, Bellaire, TX (US); Jeffrey L. Bahr, Houston, TX (US); Jiping Yang, San Jose, CA (US)

(73) Assignee: William Marsh Rice University, Houston, TX (US)

( * ) Notice: Subject to any disclaimer, the term of this patent is extended or adjusted under 35 U.S.C. 154(b) by 912 days.

(21) Appl. No.: 10/632,419

(22) Filed: Aug. 1, 2003

(65) Prior Publication Data

US 2005/0207963 A1 Sep. 22, 2005

Related U.S. Application Data

(62) Division of application No. 10/470,517, filed as application No. PCT/US02/02562 on Jan. 29, 2002, now Pat. No. 7,250,147.

(60) Provisional application No. 60/264,784, filed on Jan. 29, 2001, provisional application No. 60/272,903, filed on Mar. 2, 2001, provisional application No. 60/316,501, filed on Aug. 31, 2001, provisional application No. 60/316,521, filed on Aug. 31, 2001.

(51) Int. Cl.
*B82B 1/00* (2006.01)

(52) U.S. Cl. .................................. 423/447.2

(58) Field of Classification Search .................. 51/298, 51/307, 308, 309, 293; 451/28, 526, 539; 423/447.2, 460

See application file for complete search history.

(56) References Cited

U.S. PATENT DOCUMENTS

| 5,547,748 | A | 8/1996 | Ruoff et al. ................. 428/323 |
| 6,357,089 | B1 | 3/2002 | Koguchi et al. | |
| 7,304,103 | B2 * | 12/2007 | Tour et al. .................... 523/468 |

OTHER PUBLICATIONS

Kelly et al., Insight into the mechanism of sidewall functionalization of single-walled nanotubes: an STM study in *Chemical Physics Letters* vol. 313 pp. 445-450 Nov. 12, 1999.*
Aihara, "Lack of Superaromaticity in Carbon Nanotubes," *Journal of Physics Chem.*, vol. 98, pp. 9773-9776 (1994).
Allongue et al., "Covalent Modification of Carbon Surfaces by Aryl Radicals Generated from the Electrochemical Reduction of Diazonium Salts," *J. Am. Chem. Soc.*, vol. 119, pp. 201-207 (1997).
Chen et al., "Solution Properties of Single-Walled Carbon Nanotubes," *Science*, vol. 282, pp. 95-98 (Oct. 2, 1998).
Chen et al., "Room-temperature negative differential resistance in nanoscale molecular junctions," *Applied Physics Letters*, vol. 77, No. 8, pp. 1224-1226 (Aug. 21, 2000).
Chen et al., "Chemical attachment of organic functional groups to single-walled carbon nanotube material," *Journal of Materials Research*, vol. 13, No. 9, pp. 2423-2431 (Sep. 1998).
Cui et al., "Functional Nanoscale Electronic Devices Assembled Using Silicon Nanowire Building Blocks," *Science*, vol. 291, pp. 851-853 (Feb. 2, 2001).
Delamar et al., "Modification of Carbon Fiber Surfaces by Electrochemical Reduction of Aryl Diazonium Salts: Application to Carbon Epoxy Composites," *Carbon*, vol. 35, No. 6, pp. 801-807 (1997).
Delamar et al., "Covalent Modification of Carbon Surfaces by Grafting of Functionalized Aryl Radicals Produced from Electrochemical Reduction of Diazonium Salts," *J. Am. Chem. Soc.*, vol. 114, pp. 5883-5884 (1992).
Ebbesen et al., "Carbon Nanotubes," *Annual Review of Materials Science*, vol. 24, pp. 235-264 (1994).
Ebbesen et al., "Large-Scale Synthesis of Carbon Nanotubes," *Nature*, vol. 358, pp. 220 (Jul. 16, 1992).
Fuhrer et al., "Crossed Nanotube Junctions," *Science*, vol. 288, pp. 494-497 (Apr. 21, 2000).
Huang et al., "Directed Assembly of One-Dimensional Nanostructures into Funtional Networks," *Science*, vol. 291, pp. 630-633, (Jan. 26, 2001).
Iijima et al., "Helical microtubules of graphitic carbon," *Nature*, vol. 354, pp. 56-58 (Nov. 7, 1991).
Jost et al., "Diameter grouping in bulk samples of single-walled carbon nanotubes from optical absorption spectroscopy," *Applied Physics Letters*, vol. 75, No. 15, pp. 2217-2219 (Oct. 11, 1999).
Kosynkin et al., "Phenylene Ethynylene Diazonium Salts as Potential Self-Assembling Molecular Devices," *Organic Letters*, vol. 3, No. 7, pp. 1993-1995 (2001).

(Continued)

*Primary Examiner*—Stuart Hendrickson
(74) *Attorney, Agent, or Firm*—Winstead PC

(57) ABSTRACT

The invention incorporates new processes for the chemical modification of carbon nanotubes. Such processes involve the derivatization of multi- and single-wall carbon nanotubes, including small diameter (ca. 0.7 nm) single-wall carbon nanotubes, with diazonium species. The method allows the chemical attachment of a variety of organic compounds to the side and ends of carbon nanotubes. These chemically modified nanotubes have applications in polymer composite materials, molecular electronic applications, and sensor devices. The methods of derivatization include electrochemical induced reactions, thermally induced reactions (via in-situ generation of diazonium compounds or pre-formed diazonium compounds), and photochemically induced reactions. The derivatization causes significant changes in the spectroscopic properties of the nanotubes. The estimated degree of functionality is ca. 1 out of every 20 to 30 carbons in a nanotube bearing a functionality moiety. Such electrochemical reduction processes can be adapted to apply site-selective chemical functionalization of nanotubes. Moreover, when modified with suitable chemical groups, the derivatized nanotubes are chemically compatible with a polymer matrix, allowing transfer of the properties of the nanotubes (such as, mechanical strength or electrical conductivity) to the properties of the composite material as a whole. Furthermore, when modified with suitable chemical groups, the groups can be polymerized to form a polymer that includes carbon nanotubes.

34 Claims, 12 Drawing Sheets

OTHER PUBLICATIONS

Li et al., "Temperature dependence of the Raman spectra of single-wall carbon nanotubes," *Applied Physics Letters*, vol. 76, No. 15, pp. 2053-2055 (Apr. 10, 2000).

Liang et al., "Electronic Structures and Optical Properties of Open and Capped Carbon Nanotubes," *J. Am. Chem. Soc.*, vol. 122, pp. 11129-11137 (2000).

Liu et al., "Fullerene Pipes," *Science*, vol. 280, pp. 1253-1256 (May 22, 1998).

Nikolaev et al., "Gas-phase catalytic growth of single-walled carbon nanotubes from carbon monoxide," *Chemical Physics Letters*, vol. 313, pp. 91-97 (Nov. 5, 1999).

Obushak et al., "Arennediazonium Tetrachlorocuprates (II). Modification of the Meerwein and Sandmeyer Reactions," *Tetrahedron Letters*, vol. 39, pp. 9567-9570 (1998).

Ortiz et al., "Electrochemical modification of a carbon electrode using aromatic diazomium salts. 2. Electrochemistry of 4-nitrophenyl modified glassy carbon electrodes in aqueous media," *Journal Electroanalytical Chemistry*, vol. 455, pp. 75-81 (1998).

Rao et al., "Functionalised carbon nanotubes from solutions," *Chem. Commun.*, pp. 1525-1526 (1996).

Rao et al., "Diameter-Selective Raman Scattering from Vibrational Modes in Carbon Nanotubes," *Science*, vol. 275, pp. 187-191 (Jan. 10, 1997).

Richter et al., "Theory of Size-Dependent Resonance Raman Scattering from Carbon Nanotubes," *Physical Review Letters*, vol. 79, No. 14, pp. 2738-2740 (Oct. 6, 1997).

Saby et al., "Electrochemical Modification of Glassy Carbon Electrode Using Aromatic Diazonium Salts. 1. Blocking Effect of 4-Nitrophenyl and 4-Carboxyphenyl Groups," *Langmuir*, vol. 13, pp. 6805-6813 (1997).

Wong et al., "Covalently functionalized nanotubes as nanometre-sized probes in chemistry and biology," *Nature*, vol. 394, pp. 55-58 (1998).

Wu et al., "Finite size effects in carbon nanotubes," *Applied Physics Letters*, vol. 77, No. 16, pp. 2554-2556 (Oct. 16, 2000).

Mickelson et al, "Fluorination of Single-Wall Carbon Nanotubes", 296 Chem. Physics Letters (1998) pp. 188-194.

Mickelson E.T., "Novel Chemistry of Elemental Carbon: Graphite Fullerenes and Nanotubes", Thesis (1999).

Guo et al., "Catalytic Growth of Single-Walled Nanotubes by Laser Vaporization", 243 Chemical Physics Letters (1995) pp. 49-54.

Thess et al, "Crystalline Ropes of Metallic Carbon Nanotubes" 273 Science (1996), pp. 483-487.

Chen et al, "Solution Properties of Single-Walled Carbon Nanotubes" 282 Science (1998), pp. 95-98.

Mickelson et al., "Solvation of Fluorinated Single-Wall Carbon Nanotubes in Alcohol Solvents", 103 J. Phys. Chem. (1999), pp. 4318-4322.

Boul et al., "Reversible Sidewall Functionalization of Buckytubes", 310 Chemical Phys. Letters (1999), pp. 367-372.

Zhang et al, "Sidewall Functionalization of Single-Walled Carbon Nanotubes with Hydroxyl Group-Terminated Moieties", 16 Chem. Mater. (2004), pp. 2055-2061.

Iijima, et al, "Structural Flexibility of Carbon Nanotubes", J. Chem. Phys., 104:1996, pp. 2089-2092.

* cited by examiner

1

2

3

4

5

6

7

8

9

11

12 a) TosCl, H₂O, THF  b) 4-nitrophenol, DMF, K₂CO₃  c) H₂, Pd/C  d) NOBF₄, CH₃CN

A

B

16, R = Cl
17, R = tert-butyl
18, R = CO₂CH₃
19, R = NO₂
20, R = COOH

21, R = (ester linkage to long chain alcohol)

cured epoxy (thermoset) resin

US 7,691,359 B2

CARBON NANOTUBES DERIVATIZED WITH DIAZONIUM SPECIES

PRIORITY BENEFIT AND CROSS REFERENCE TO RELATED APPLICATIONS

This Application is a Divisional Application of the U.S. patent application Ser. No. 10/470,517, filed on Jul. 29, 2003, a 371 National Phase Application of International Application No. PCT/US02/02562, filed Jan. 29, 2002, which application claims priority benefits to U.S. patent application Ser. Nos. (1) 60/264,784, filed Jan. 29, 2001; (2) 60/272,903, filed Mar. 2, 2001; (3) 60/316,501, filed on Aug. 31, 2001; and (4) 60/316,521 filed Aug. 31, 2001, all of which are hereby incorporated by reference.

The present invention was made in connection with research pursuant to grant numbers NASA-JSC-NCC 9-77 from the National Aeronautics and Space Administration; grant number NSR-DMR-0073046 from the National Science Foundation; and grant number N00014-99-1-0406 from the DARPA/ONR.

FIELD OF INVENTION

The present invention relates broadly to carbon nanotubes. More specifically, the invention relates to derivatization of carbon nanotubes with diazonium compounds and to uses for the derivatized carbon nanotubes.

BACKGROUND OF THE INVENTION

Fullerenes are closed-cage molecules composed entirely of $sp^2$-hybridized carbons, arranged in hexagons and pentagons. Fullerenes (e.g., $C_{60}$) were first identified as closed spheroidal cages produced by condensation from vaporized carbon. Fullerene tubes are produced in carbon deposits on the cathode in carbon arc methods of producing spheroidal fullerenes from vaporized carbon. Ebbesen et al. (Ebbesen I), "Large-Scale Synthesis Of Carbon Nanotubes," *Nature*, Vol. 358, p. 220 (Jul. 16, 1992) and Ebbesen et al., (Ebbesen II), "Carbon Nanotubes," *Annual Review of Materials Science*, Vol. 24, p. 235 (1994). Such tubes are referred to herein as carbon nanotubes. Many of the carbon nanotubes made by these processes were multi-wall nanotubes, i.e., the carbon nanotubes resembled concentric cylinders. Carbon nanotubes having up to seven walls have been described in the prior art. Ebbesen II; Iijima et al., "Helical Microtubules Of Graphitic Carbon," *Nature*, Vol. 354, p. 56 (Nov. 7, 1991).

Since 1991, there has been a great deal of interest in derivatization of carbon nanotubes, and more, particularly, single-wall carbon nanotubes, to facilitate their manipulation, to enhance the solubility of such nanotubes, and to make the nanotubes more amenable to composite formation. This is because single-wall carbon nanotubes are one of the more striking discoveries in the chemistry and materials genre in recent years. Nanotubes posses tremendous strength, an extreme aspect ratio, and are excellent thermal and electrical conductors. A plethora of potential applications for nanotubes have been hypothesized, and some progress is being made towards commercial applications. Accordingly, chemical modification of single-wall carbon nanotubes, as well as multi-wall carbon nanotubes, will be necessary for some applications. For instance, such applications may require grafting of moieties to the nanotubes: to allow assembly of modified nanotubes, such as single-wall carbon nanotubes, onto surfaces for electronics applications; to allow reaction with host matrices in composites; and to allow the presence of a variety of functional groups bound to the nanotubes, such as single-wall carbon nanotubes, for sensing applications.

While there have been many reports and review articles on the production and physical properties of carbon nanotubes, reports on chemical manipulation of nanotubes have been slow to emerge. There have been reports of functionalizing nanotube ends with carboxylic groups (Rao, et al., *Chem. Commun.*, 1996, 1525-1526; Wong, et al., *Nature*, 1998, 394: 52-55), and then further manipulation to tether them to gold particles via thiol linkages (Liu, et al., *Science*, 1998, 280: 1253-1256). Haddon and co-workers (Chen, et al., *Science*, 1998, 282:95-98) have reported solvating single-wall carbon nanotubes by adding octadecylamine groups on the ends of the tubes and then adding dichlorocarbenes to the nanotube sidewall, albeit in relatively low quantities (~2%).

Success at covalent sidewall derivatization of single-wall carbon nanotubes has been limited in scope, and the reactivity of the sidewalls has been compared to the reactivity of the basal plane of graphite. Aihara, J. *J. Phys. Chem.* 1994, 98, 9773-9776. A viable route to direct sidewall functionalization of single-wall carbon nanotubes has been fluorination at elevated temperatures, which process was disclosed in a co-pending application commonly assigned to the assignee of the Application, U.S. patent application Ser. No. 09/810,390, "Chemical Derivatization Of Single-Wall Carbon Nanotubes To Facilitate Solvation Thereof; And Use Of Derivatized Nanotubes To Form Catalyst-Containing Seed Materials For Use In Making Carbon Fibers," to Margraves et al., filed Mar. 16, 2001. These functionalized nanotubes may either be de-fluorinated by treatment with hydrazine or allowed to react with strong nucleophiles, such as alkyllithium reagents. Although fluorinated nanotubes may well provide access to a variety of functionalized materials, the two-step protocol and functional group intolerance to organolithium reagents may render such processes incompatible with certain, ultimate uses of the carbon nanotubes. Other attempts at sidewall modification have been hampered by the presence of significant graphitic or amorphous carbon contaminants. Chen, Y. et al., *J. Mater Res.* 1998 13, 2423-2431.

It would thus be desirable to develop a direct approach to high degrees of functionalization of nanotubes that would be accommodating (i.e. a one step approach and one that is compatible with certain, ultimate uses of the nanotubes). Such uses include applications to utilize the tremendous strength, extreme aspect ratios, and excellent thermal and electrical conductive properties of the nanotubes.

Accordingly, it is an object of this invention to provide a method for derivatizing carbon nanotubes, especially the sidewalls and end-caps of single-wall carbon nanotubes, utilizing chemistries that are direct, accommodating, and compatible with the ultimate uses and applications of the nanotubes.

SUMMARY OF THE INVENTION

The invention incorporates new processes for the chemical modification of carbon nanotubes. Such processes involve the derivatization of multi- and single-wall carbon nanotubes, including small diameter (ca. 0.7 nm) single-wall carbon nanotubes, with diazonium species. The method allows the chemical attachment of a variety of organic compounds to the side and ends of carbon nanotubes. These chemically modified nanotubes have applications in polymer composites, molecular electronic applications, and sensor devices. The methods of derivatization include electrochemical induced reactions, thermally induced reactions (via in-situ generation of diazonium compounds or via preformed diazonium compounds), and photochemically induced reactions. The derivatization causes significant changes in the spectroscopic properties of the nanotubes. The estimated degree of functionality is ca. 1 out of every 20 to 30 carbons in a nanotube bearing a functionality moiety.

The electrochemical induced processes include procedures utilizing an assembly of nanotubes, such as a piece of "bucky paper" or mat, which can be held with a silver paste covered alligator clip and immersed in an acetonitrile solution of a diazonium salt and a supporting electrolyte salt, while applying a potential (typically a negative potential) to the assembly of nanotubes. By such a process, a molecular wire (such as an oligo(phenylene ethynylene) molecular wire) and also a molecular electronic device have been covalently attached to a nanotube. This represents the marriage of wire-like nanotubes with molecular wires and with molecular electronic devices.

Such electrochemical processes can be adapted to apply site-selective chemical functionalization of nanotubes. Moreover, it allows for the controlled attachment of two or more different chemical functionalities to different locations on the nanotubes.

The thermally induced processes include procedures in which a dispersion of carbon nanotubes in an organic solvent mixture is treated with a precursor to a reactive diazonium species. This precursor is then transformed in-situ to the reactive species, and its thermal decomposition leads to chemical attachment to the carbon nanotubes. It is believed that such a process has the advantage of scalability and avoids the necessity of isolating and storing potentially unstable diazonium compounds, i.e., the species that reacts with the carbon nanotubes.

Moreover, the thermal induced processes also include procedures utilizing pre-formed diazonium species. The reactive species can be prepared beforehand, isolated, and added to the mixture. Additional variations include variations in the temperature of the process (ambient temperature and higher and lower temperatures), ratio of reactants, and a variety of organic solvents.

The photochemical induced processes are similar to the thermal induced reaction except that a photochemical process (not a thermal process) is utilized to cause the decomposition of the diazonium species that leads to the chemical attachment of the moieties to the carbon nanotubes.

When modified with suitable chemical groups, the nanotubes are chemically compatible with a polymer matrix, allowing transfer of the properties of the nanotubes (such as mechanical strength) to the properties of the composite material as a whole. To achieve this, the modified carbon nanotubes can be thoroughly mixed (physically blended) with the polymeric material, and/or, if desired, allowed to react at ambient or elevated temperature. These methods can be utilized to append functionalities to the nanotubes that will further covalently bond to the host polymer matrix, or directly between two tubes themselves.

There are a multitude of variations in the chemical structure of the polymer matrix, i.e., polyethylene, various epoxy resins, polypropylene, polycarbonate etc. In general, possible composite materials could be made with chemically modified nanotubes and thermoplastics, thermosets, elastomers, and others. There is also a host of variations possible in the chemical groups that can be attached to the nanotubes. The specific group will be chosen to enhance compatibility with the particular polymer matrix desired and, if desired, to cause chemical bonding to the host material.

Furthermore, when modified with suitable chemical groups, the nanotubes can be used as a generator of polymer growth. i.e., the nanotubes would be derivatized with a functional group that could be an active part of a polymerization process, which would also result in a composite material in which the carbon nanotubes are chemically involved.

DESCRIPTION OF ILLUSTRATIVE EMBODIMENTS

Figure 1:
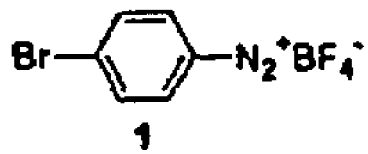
FIG. 1 shows the structure of certain aryl diazonium salts used to derivatize single-wall carbon nanotubes.
Figure 1:
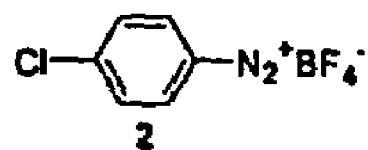
Figure 1:
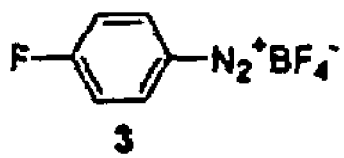
Figure 1:
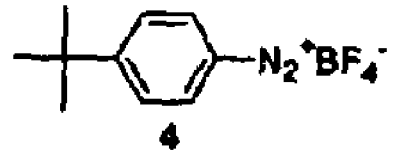
Figure 1:
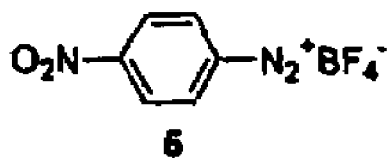
Figure 1:
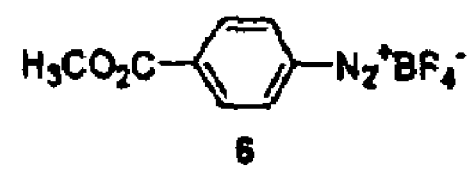
Figure 1:
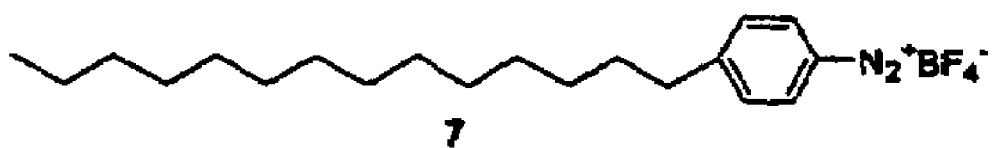
Figure 1:
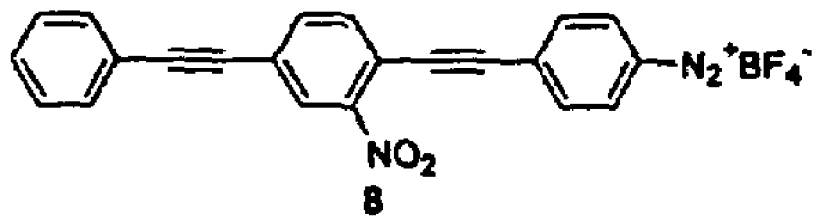
Figure 1:
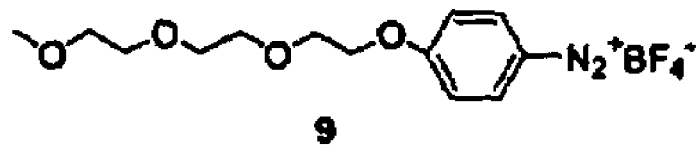
Figure 1:
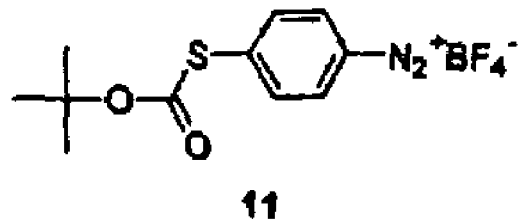
Figure 1:
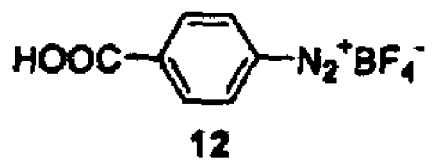

Electrochemical Derivatization of Carbon Nanotubes with Diazonium Species

Aryl diazonium salts are known to react with electron deficient olefins, known as the Meerwein reaction. Obushak, M. D., et al., *Tett. Lett.* 1998, 39, 9567-9570. In such solution phase reactions, diazonium salt decomposition is typically catalyzed by a metal salt such as copper(I) chloride, giving a reactive aryl radical. In some cases, the reaction is believed to proceed through an aryl cation. This type of chemistry has been successfully applied to the modification of carbon surfaces via grafting of electrochemically reduced aryl diazonium salts. Delamar, M., et al., *Carbon* 1997, 35, 801-807; Allongue, P., et al., *J. Am Chem. Soc.* 1997, 119, 201-207; Ortiz, B., et al., *J. Electro. Chem.* 1998, 455, 75-81; Saby, C., et al., *Langmuir* 1997, 13, 6805-6813; Delamar, M, et al., *J. Am. Chem. Soc.* 1992, 114, 5883-5884. Reduction may give an aryl radical that covalently attaches to the carbon surface. This technique has been applied to both highly ordered pyrolitic graphite (HOPG) and glassy carbon (GC) electrodes.

Methylene chloride and acetonitrile were distilled from calcium hydride. Dimethylformamide was distilled and stored over molecular sieves. Tetrahydrofuran was distilled from sodium/benzophenone ketyl. All other reagents were obtained commercially and used without further purification.

Carbon Nanotubes. A method for producing small diameter (ca. 0.7 nm) single-wall carbon nanotubes has been developed by Smalley, et al. Nikolaev, P., et al., *Chem. Phys. Lett.* 1999, 313, 91-97. This method is disclosed in a co-pending application commonly assigned to the assignee of the Application, U.S. patent application Ser. No. 09/830,642 "Gas-Phase Nucleation and Growth of Single-Wall Carbon Nanotubes from High Pressure CO," to Smalley et al., filed Apr. 27, 2001, which is incorporated herein by reference. This material is now commercially available (Carbon Nanotechnologies Inc., HiPco material). As the diameter of these nanotubes is approximately the same as that of $C_{60}$, these nanotubes are understood to display enhanced reactivity relative to the larger diameter tubes typically produced by laser oven methods, since the reactivity of $C_{60}$ has been attributed in part to curvature strain. While the present invention is also pertinent to multi-wall carbon nanotubes and larger diameter single-wall carbon nanotubes, these small diameter nanotubes were primarily utilized during the examples demonstrating the present process. A variety of diazonium salts have been used, including those that provide moieties conducive to further elaboration after attachment of the nanotubes. Also, an oligo (phenylene ethynylene) molecular device similar to the one that has been shown to exhibit memory and room temperature negative resistance (Chen, J. et al., *App. Phys. Lett.* 2000, 77, 1224-1226) has been attached to the nanotubes.

The following examples, as well as, the other examples described herein, are presented to further illustrate the invention and, are not to be construed as unduly limiting the scope of this invention.

A. EXAMPLES NOS. 1-11

For the electrochemical derivatization experiments, a piece of bucky paper, formed by filtration of a suspension, was used as the working electrode in a 3-electrode cell and immersed in an acetonitrite solution containing the diazonium salt and an electrolyte. The diazonium salts were probably reduced to aryl radicals at the surface of the bucky paper, and subsequently become covalently attached to the nanotubes. The conductivity of single-wall carbon nanotubes has been well documented. In general, aryl diazonium salts are easily prepared under conditions that tolerate a variety of functional groups. Consequently, the method described herein allows functionalization of nanotubes with a wide variety of diazonium salts, including those that provide chemical handles for additional elaboration after attachment to nanotubes.

Figure 2:
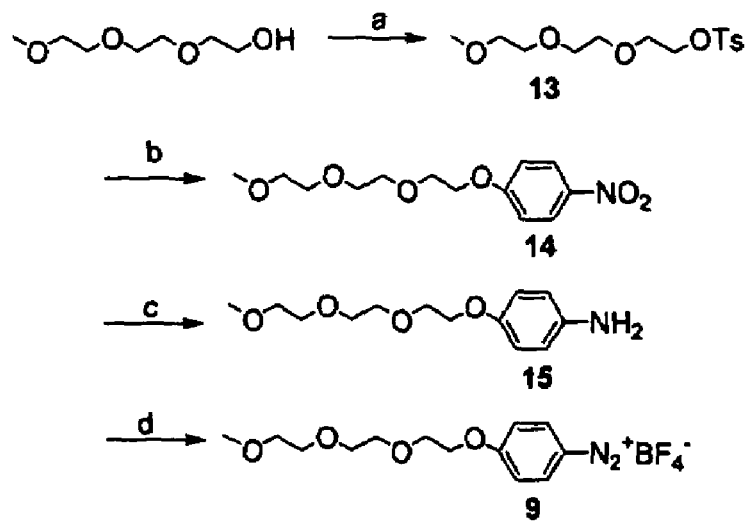
FIG. 2 shows the scheme utilized to prepare Compounds 9 and 11 as reflected in FIG. 1.
Figure 2:
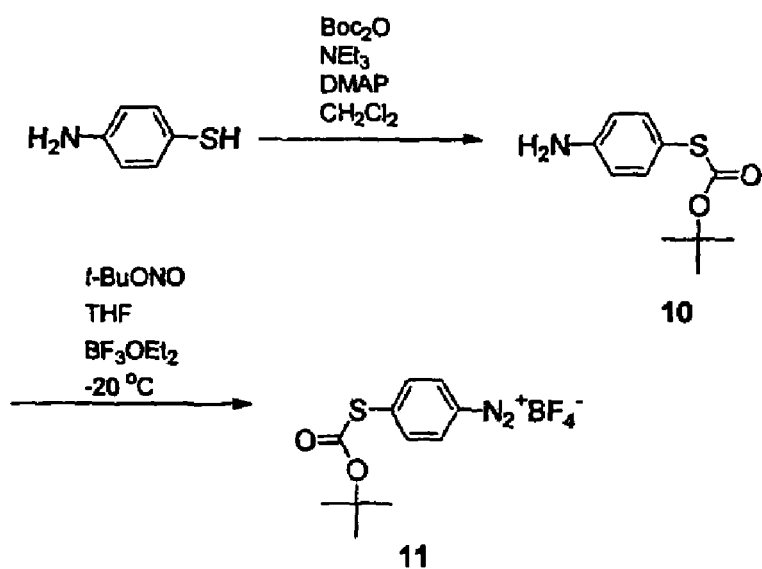

The purified single-wall nanotubes (hereafter, SWNT-p) used in this investigation contained little amorphous or other extraneous carbon contaminants. The purification technique for the nanotubes is discussed in more detail below. The fact the SWNT-p contained little amorphous or other extraneous carbon contaminants is significant, as the presence of such material may have hindered the ability to determine whether previous derivatization efforts were successful. (While the lack of impurities was an issue in the initial demonstrations respecting the operability of the reactions, it should be noted that these reactions will work on raw, impurified multi- and single-wall carbon nanotubes, i.e. the reactions will work even in the absence of a purification process.) In addition, the residual iron content (catalyst from the gas-phase growth technique) was <1 atomic % by electron microprobe analysis (EMPA) (ca. 0.3 atomic %). The diazonium salts used to derivatize SWNT-p are shown in FIG. 1. Compounds 1-7 and 11 were prepared from the corresponding aniline derivatives by known methods (Kosynkin, D.; Tour, J. M. *Org. Lett.* 2000), using nitrosonium tetrafluoroborate as the diazotization reagent. Compound 8 was prepared using the process reported in Kosynkin, D., et al., *Org. Lett.* 2001, 3, 993-995. Compound 9 and 10 were prepared according to scheme reflected in FIG. 2. Characterization of these compounds is further discussed below. Reaction of these compounds with SWNT-p generated SWNT-x, where x=1-9 and 11-12, respectively.

The small diameter single-wall carbon nanotubes used in this investigation were produced by a gas-phase catalytic technique, using carbon monoxide as the feedstock and iron carbonyl as the catalyst. Nikolaev, P., et al., *Chem. Phys. Lett.* 1999, 313, 91-97; U.S. patent application Ser. No. 09/830, 642. (These carbon nanotubes are now commercially available; Carbon Nanotechnologies Inc., HiPco material). The raw production material was purified by air oxidation at 150° C. for a period of 12 hours, followed by annealing in argon at 800° C. for 6 hours. This material was sonicated in concentrated hydrochloric acid (ca. 30 mg in 60 mL), filtered, washed extensively with water and 2-propanol, and dried under vacuum. The purity of these samples was verified by SEM, TEM, and EMPA.

Bucky Paper. The use of bucky paper as a working electrode for the derivatization raises several unique issues. Electrical contact between the source and the bucky paper during the electrochemical process is an issue. This situation can be improved by application of colloidal silver paste to the alligator clip used to hold the bucky paper. It is also believed that the success of the reaction is at least partially dependent on the quality of the bucky paper employed as the working electrode. Accordingly, it was helpful to achieve a suspension that contained little or no visible particulate prior to filtration to form the bucky paper.

General procedure for diazotization of aniline derivatives. A portion of nitrosonium tetrafluoroborate (1.2 molar equivalents) was weighed out in a glove box and sealed. After removal from the glove box, acetonitrile was added (3 mL/mmol of aniline), and the solution was cooled to −30° C. A solution of the aniline derivative (1 molar equivalent) in acetonitrile (ca. 1 mL/mmol) was added dropwise while stirring (vide infra). In some cases, dry methylene chloride was used as a co-solvent for the aniline derivative. After complete addition, stirring was continued for 30 minutes, at which time the cold bath was removed. After stirring for a total of 1 hour, the solution was diluted with a 2× volume of ether and stirred. The precipitate was collected by filtration and washed with ether.

4-Bromobenzenediazonium tetrafluoroborate (1). Yield: 85%. MP 138° C. $^1$H NMR (400 MHz, CD$_3$CN) δ 8.22 (ABq, J=9.1 Hz, Δv=102.1 Hz, 4H).

4-Chlorobenzenediazonium tetrafluoroborate (2). Yield: 78%. MP 134° C. $^1$H NMR (400 MHz, CD$_3$CN) δ 8.24 (ABq, J=9.2 Hz, Δv=214.2 Hz, 4H).

4-Fluorobenzenediazonium tetrafluoroborate (3). Yield: 79%. MP 160° C. $^1$H NMR (400 MHz, CD$_3$CN) δ 8.64 (dd, J=9.4 Hz, 9.5 Hz, 2H), 7.69 (dd, J=9.4 Hz, 9.5 Hz, 2H).

4-tert-Butylbenzenediazonium tetrafluoroborate (4). The 4-tert-butylaniline was dissolved in a 1:1 mixture of acetonitrile and dry methylene chloride prior to addition to the nitrosonium tetrafluoroborate. Yield: 78%. MP 91° C. IR (KBr) 3364.8, 3107.3, 2968.6, 2277.2, 1579.2, 1482.0, 1418.0, 1373.5, 1269.8, 1056.9, 841.1, 544.6, 621.4 cm$^1$. $^1$H NMR (400 MHz, CD$_3$CN) δ 8.16 (ABq, J=9.0 Hz, Δv=298.7 Hz, 4H), 1.30 (s, 12H). $^{13}$C NMR (100 MHz, CD$_3$CN) δ 168.85, 133.67, 130.43, 111.88, 37.86, 30.84.

4-Nitrobenzenediazonium tetrafluoroborate (5). Yield: 67%. MP 142° C. $^1$H NMR (400 MHz, CD$_3$CN) δ 8.72 (ABq, J=9.4 Hz, Δv=65.4 Hz, 4H).

4-Methoxycarbonylbenzenediazonium tetrafluoroborate (6). Yield 80%; MP 113° C. IR (KB$_r$) 3103.8, 3042.4, 2955.3, 2294.7, 2310.1, 1731.4, 1582.9, 1439.5, 1306.4, 1045.23, 953.1, 860.9, 758.5, 666.3, 528.0 cm$^{-1}$. $^1$H NMR (400 MHz CD$_3$CN) δ 8.51 (AB$_9$, J=9.1 Hz, Δv=77.9 Hz, 4H), 3.97 (s, 3H). 13C NMR (100 MHz, CD$_3$CN) 165.02, 142.44, 134.12, 133.16, 119.77, 54.43.

4-Tetradecylbenzenediazonium tetrafluoroborate (7). The 4-tetradecylaniline was dissolved in a 1:1 mixture of acetonitrile and dry methylene chloride prior to addition to the nitrosonium tetrafluoroborate. Yield: 69%. MP 82° C. IR (KBr) 3103.8, 2919.5, 2289.6, 1577.8, 1473.7, 1070.8, 1024.8, 844.5, 813.8, 716.9, 541.0, 510.2 cm$^{-1}$. IR (KBr) 3103.8, 2919.5, 2289.6, 1577.8, 1473.7, 1070.8, 1024.8, 844.5, 813.8, 716.9, 541.0, 510.2 cm$^1$. $^1$H NMR (400 MHz, CDCl$_3$) δ8.02 (ABq, J=8.8 Hz, Δv=370.6 Hz, 4H), 2.76 (t, J=7.7 Hz, 2H), 1.61 (quin, J=7.8 Hz, 2H), 1.23 (s, 22H), 0.85 (t, J=7.0 Hz, 3H). $^{13}$C NMR (100 MHz, CDCl$_3$) δ 159.92, 133.26, 131.94, 110.96, 37.49, 32.34, 30.87, 30.12, 30.10, 30.07, 30.04, 29.91, 29.78, 29.75, 29.72, 23.11, 14.55.

2-[2-(2-methoxyethoxy)ethoxy]ethyl p-toluenesulfonate (13). Sodium hydroxide (3.65 g, 91.3 mmol) and tri(ethylene glycol)monomethyl ether (10.0 g, 60.9 mmol) were dissolved in a mixture of tetrahydrofuran and water (140 mL, 20 mL, respectively). The solution was cooled in an ice bath. A solution of toluenesulfonyl chloride (12.76 g, 67.0 mmol) in 20 mL of tetrahydrofuran was added slowly. The solution was stirred at 0° C. for 3 hours, then poured into 50 mL of ice water. The mixture was extracted several times with methylene chloride. The combined organic layers were washed with dilute HCl, then brine, and dried over magnesium sulfate. After filtration, the solvent was removed by distillation at reduced pressure to give 16.6 g of the product (86% yield). $^1$H NMR (400 MHz, CDCl$_3$) δ 7.50 (ABq, J=7.9 Hz, Δv=179 Hz, 4H), 4.09 (app t, J=4.8 Hz, 2H), 3.61 (app t, J=4.9 Hz, 2H), 3.55 to 3.52 (m, 6H), 3.47 to 3.46 (m, 2H), 3.30 (s, 3H), 2.38 (s, 3H). $^{13}$C NMR (100 MHz, CDCl$_3$) δ 145.21, 133.28, 130.21, 128.28, 72.20, 71.00, 70.85, 69.69, 68.95, 68.26, 59.31, 21.96. IR (neat) 3503.3, 2878.5, 1597.9, 1453.1, 1356.3, 1292.0, 1247.0, 1177.2, 1097.5, 1019.0, 924.17, 818.0, 776.9, 664.5 cm$^{-1}$.

4-{2-[2-(2-methoxyethoxy)ethoxy]ethyl}nitrobenzene (14). A portion of 13 (9.0 g, 28.3 mmol) was dissolved in 50 mL of dimethylformamide. Potassium carbonate (11.75 g, 85.0 mmol) and 4-nitrophenol (3.82 g, 27.5 mmol) were added. The solution was stirred at 80° C. for 16 hours. After cooling to room temperature, the solution was poured into water and extracted three times with methylene chloride. The combined organic layers were washed with water, then brine, dried over magnesium sulfate, filtered, and the solvent was removed by distillation at reduced pressure. Chromatography (silica, hexane:ethyl acetate, 1:2) was employed to isolate the product (5.71 g, 73% yield). IR (neat) 3109.2, 3078.2, 2878.5, 1726.3, 1588.1, 1511.2, 1337.1, 1106.7, 1050.3, 932.6, 845.5, 753.3, 656.1 cm$^{-1}$. $^1$H NMR (CDCl$_3$) δ 8.07 (d, J=9.3 Hz, 2H), 6.88 (d, J=9.3 Hz, 2H), 4.12 (app t, 2H), 3.79 (app t, 2H), 3.62 (m, 2H), 3.58 to 3.53 (m, 4H), 3.44 to 3.42 (m, 2H), 3.26 (s, 3H); $^{13}$C NMR (100 MHz, CDCl$_3$) δ 164.29, 141.93, 126.24, 114.99, 72.29, 71.29, 71.03, 70.98, 69.77, 68.60, 59.44.

4-{2-[2-(2-methoxyethoxy)ethoxy]ethyl}aniline (15). A portion of 14 (5.77 g, 20.2 mmol) was dissolved in 40 mL of acidic ethanol, and a catalytic amount of 10% palladium on carbon was added. The mixture was hydrogenated on a Parr apparatus (60 psi, 70° C.) for 3 hours. The mixture was then filtered over Celite, washing with ethanol. Solid sodium bicarbonate was added, and the mixture was stirred for 2 hours and, then filtered. The solvent was removed by distillation at reduced pressure, leaving a brown oil (5.0 g, 98% yield). IR (neat) 3441.82, 3349.64, 2893.88, 2238.41, 1634.41, 1516.36, 1449.79, 1234.71, 1101.56, 906.97, 722.62 cm$^{-1}$. $^1$H NMR (400 MHz, CDCl$_3$) δ 6.65 (ABq, J=8.7 Hz, Δv=51.5 Hz, 4H), 4.01 (t, J=5.4 Hz, 2H), 3.77 (t, J=4.6 Hz, 2H), 3.69 (app t, J=5.6 Hz, 2H), 3.65 to 3.59 (m, 4H), 3.51 (app t, J=4.9 Hz, 2H), 3.34 (s, 3H), 3.0 (brs, 2H). $^{13}$C NMR (100 MHz, CDCl$_3$) δ 152.30, 140.58, 116.75, 116.24, 72.31, 71.14, 71.02, 70.93, 70.30, 68.49, 59.44.

4-{2-[2-(2-methoxyethoxy)ethoxy] ethyl}benzenediazonium tetrafluoroborate (9). Compound 15 was subjected to the procedure described above for diazotization. The product was not crystalline, but rather a dark red, sticky material that was difficult to manipulate. The residue was mixed three times with ether, decanting the solvent. This material was sufficiently pure by $^1$H NMR, and was used without further purification or characterization (2.17 g, 52% yield). $^1$H NMR (400, MHz, acetone-d$_6$) δ 8.12 (ABq, J=9.5 Hz, Δv=479.5 Hz, 4H), 4.53 (app t, J=4.5 Hz, 2H), 3.92 (t, J=4.4 Hz, 2H), 3.68 to 3.66 (m, 2H), 3.61 to 3.56 (m, 4H), 3.46 (t, J=5.4 Hz, 2H), 3.27 (s, 3H).

Compound 10. To a screw-cap tube with a magnetic stir bar was added Boc$_2$O (17.6 g, 80.6 mmol), 4-aminothiophenol (10.0 g, 80.6 mmol), triethylamine (13.5 mL, 96.7 mmol), 150 mL of dichloromethane, and N,N-dimethylaminopyridine (4.92 g, 40.3 mmol). The tube was flushed with nitrogen, and the screw-cap was installed. The solution was stirred at room temperature for 24 h. The solution was then washed with three 75 mL portions of water, the organic layer was dried over magnesium sulfate, then filtered and concentrated. The residue was chromatographed on silica using hexanes:ethyl acetate (1.5:1) as the eluant. The product was isolated as a clear oil that crystallized on standing (16.16 g, 94%). mp 83-86° C. IR (KBr) 3454.5, 3376.8, 2978.6, 1711.4, 1630.1, 1597.4, 1500.0, 1384.4, 1296.0, 1201.0, 1176.3, 1125.4, 857.2, 825.2, 669.8 cm$^{-1}$. $^1$H NMR (200 MHz, CDCl$_3$) δ 7.32 (d, J=8.6 Hz, 2H), 6.70 (d, J=8.6 Hz, 2H), 3.83 (brs, 1H), 4.54 (s, 9H). $^{13}$C NMR (50 MHz, CDCl$_3$) 169.72, 148.26, 137.05, 116.33, 115.89, 85.49, 28.63.

Compound 11. To a 500 mL round bottom flask cooled to −20° C. was added 6.74 mL of BF$_3$OEt$_2$ (171.9 mmol). To this was added a solution of 10 (3.0 g, 225.3 mmol) dissolved in 30 mL of THF, over a period of 10 min. To this was added a solution of t-butylnitrite (5.59 mL, 103.12 mmol) in 20 mL of THF. The solution was stirred and allowed to warm to 0° C. over 40 min, at which time 400 mL of cold ether was added. The precipitate was collected by filtration, to obtain 4.14 g (96%) of the desired product. $^1$H NMR (400 MHz, CD$_3$CN) δ 8.52 (d, J=9.1 Hz, 2H), 8.0 (d, J=9.1 Hz, 2 H), 1.54 (s, 9H).

4-hydroxycarbonylphenyldiazonium tetrafluoroborate (12). This compound was prepared according to the general procedure (vide supra). Sulfolane was used as a co-solvent for the 4-aminobenzoic acid. Yield: 60%. IR (KBr) 3247.9, 3105.3, 2305.5, 1732.6, 1416.1, 1386.5, 1300.1, 1232.8, 1093.1, 996.1, 906.9, 872.0, cm$^{-1}$. $^1$H NMR (400 MHz, CD$_3$CN) δ 8.64 (d, J=9.0 Hz, 2H), 8.44 (d, J=9.0 Hz, 2H).

General procedure for electrochemical derivatization of SWNT-p. The apparatus used for the electrochemical derivatization experiments was a 3-electrode cell, with Ag/AgNO$_3$ reference electrode and platinum wire counter electrode. A piece of bucky paper (1-2 mg) served as the working electrode. The bucky paper was prepared by filtration of a 1,2-dichlorobenzene suspension over a 0.2 μM PTFE (47 mm, Sartorius) membrane. After drying under vacuum, the paper was peeled off the membrane, and a piece was excised for use in the derivatization. The bucky paper was held with an alligator clip, previously treated with colloidal silver paste (Ted Pella, Inc.), and immersed in an acetonitrile solution of the diazonium salt (0.5 mM for SWNT-1-SWNT-7 and SWNT-9; 0.01 M for SWNT-8) and tetra-n-butylammonium tetrafluoroborate (0.05 M). Care was taken not to immerse the alligator clip itself. A potential of −1.0 V was applied for a period of 30 min. Care was taken for the exclusion of light, and nitrogen was bubbled through the solution during the experiment. After reaction, the portion of the bucky paper that was not immersed in the solution was excised, and the remainder was soaked in acetonitrile for 24 hours, then washed with acetonitrile, chloroform, and ethanol. After drying, this material was sonicated in acetonitrile for 20 minutes, filtered, and washed again with acetonitrile, 2-propanol, and chloroform. The reaction products were dried under vacuum at room temperature prior to characterization. Control experiments without a diazonium salt confirm that such conditions do not affect the nanotubes, as verified by UV/vis/NIR, Raman, and TGA.

Other salts and parameters. A great variety of aryl diazonium salts for modification can be utilized in the process of the invention. Additionally, parameters such as added potential, the duration of the applied potential, the solvent, and the supporting electrolyte can be varied. Furthermore, alkyl, alkenyl and alkynyl additions could be used for the process of the invention.

B. Characterization

Scanning electron microscopy (SEM) experiments were performed on a Phillips ESEM XL-30, at an accelerating voltage of 50,000 V. This instrument was equipped with an EDAX detector. Samples for TEM imaging were drop dried from THF onto a 200 mesh lacey carbon grid on a copper support. The accelerating voltage was 100 K.V. Raman spectra were collected on a Renishaw Ramascope, on solid samples, with excitation at 782 nm. UV/Vis/NIR absorption spectra were collected on a Shimadzu UVPC-3101, in double beam mode, with solvent reference. FT-IR spectra were collected using an attenuated total reflectance (ATR) accessory. TGA data were collected in argon, on a TA Instruments SDT-2960. AFM experiments were performed in tapping mode on a Digital Multi-mode SPM. Samples for these experiments were dispersed by sonication and spin coated on a freshly cleaved mica substrate. EMPA experiments were performed on a Cameca SX-50. The instrument was calibrated, and data were taken from several different points on each sample. The average of these points is reported below. NMR data were collected on a Bruker Avance 400. Chemical shifts are reported in ppm downfield from TMS, and referenced to solvent. Melting points are not corrected.

Figure 3:
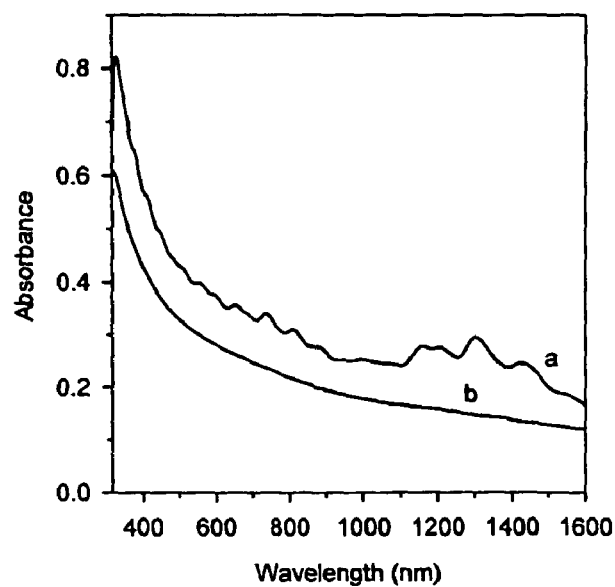
FIG. 3 shows the absorption spectra in dimethylformamide for (A) SWNT-p and (B) SWNT-1.
Figure 4:
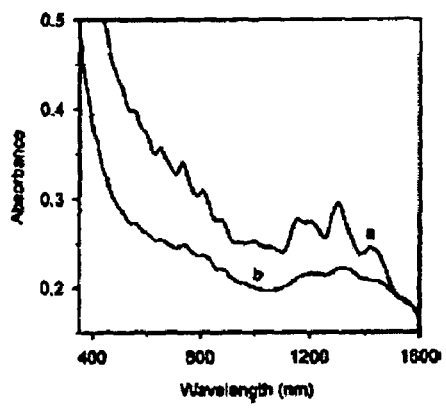
FIG. 4 shows the absorption spectra in dimethylformamide for (A) SWNT-p and (B) SWNT-8.

Electronic Structure and Optical Properties. The electronic structure and optical properties of single-wall carbon nanotubes have been well investigated. Liang, W. Z., et al., *J. Am. Chem. Soc.* 2000, 122, 11129-11137; Jost, O., et al., *App. Phys. Lett.* 1999, 75, 2217-2219; Wu, J., et al., *App. Phys. Lett.* 2000, 77, 2554-2556. The UV/VIS/NIR absorption spectrum of SWNT-p and SWNT-1 is shown in FIG. 3. The features (van Hove bands) in the spectrum of SWNT-p are due to singularities in the density of states (DOS), and, in this spectral region, are attributed to the band gap transitions in semiconducting nanotubes. The width of these features is due to the overlap of features from tubes of different diameters and chiral indices. These transitions are no longer visible for SWNT-1, and the spectrum is essentially featureless. The absorption spectra of SWNT-2-SWNT-7 and SWNT-11-SWNT-12 are similar, with no apparent features. The spectra of SWNT-8 (FIG. 4) and SWNT-9 retained some visible features, but these were significantly reduced relative to SWNT-p. The loss of structure in the absorption spectra is indicative of significant electronic perturbation of the nanotubes and disruption of the extended rr network. This effect is most consistent with covalent functionalization rather than simple adsorption to nanotube walls or end caps.

Figure 5:
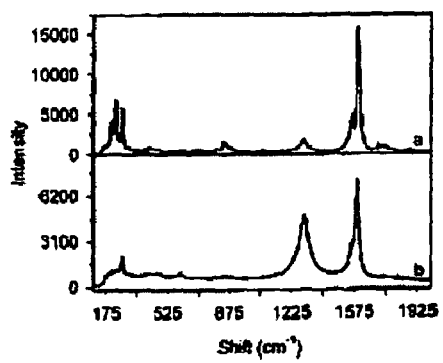
FIG. 5 shows the Raman spectra from solid samples, with excitation at 782 nm, for (A) SWNT-p and (B) SWNT-1.

Raman Spectroscopy. Raman spectroscopy of single-wall carbon nanotubes is also well developed both theoretically and experimentally. Richter, E., et al., *Phys. Rev. Lett.* 1997, 79, 2738-2740; Rao, A. M, et al., *Science* 1997, 275, 187-191; Li, H. D., et al., *App. Phys. Lett.* 2000, 76, 2053-2055. The Raman spectrum of SWNT-p (FIG. 5A) displays two strong bands; the radial breathing ($\omega_r$~230 cm$^{-1}$) and tangential ($\omega_t$~1590 cm$^{-1}$) modes. The multiple peaks seen in the radial breathing mode are presumably due to the distribution of tube diameters in the sample. The weaker band centered at ca. 1290 cm$^{-1}$ ($\omega_d$) is attributed to disorder or sp$^3$-hybridized carbons in the hexagonal framework of the nanotube walls. The minor band at 850 cm$^{-1}$ is also characteristic of these small diameter nanotubes, although its molecular origin is not certain. The spectrum of SWNT-1 (FIG. 5B) is quite different. Notably, the relative intensity of the disorder mode is much greater. This is a result of the introduction of covalently bound moieties to the nanotube framework, wherein significant amounts of the sp$^2$ carbons have been converted to sp$^3$-hybridization. The Raman spectra of the other functionalized materials display similar modifications, relative to SWNT-p, but to different degrees. The frequency of the disorder mode and the relative intensities of the three major bands are shown in Table 1.

TABLE 1

Disorder mode frequency and intensity ratios
Of major peaks in Raman Scattering Experiments

| Compound | $\omega_d$ | Int. Ratio$(\omega_r:\omega_d:\omega_t)^{a,b}$ |
|---|---|---|
| SWNT-p | 1291 | 1.0:0.3:2.7 |
| SWNT-1 | 1295 | 1.0:2.2:3.3 |
| SWNT-2 | 1294 | 1.0:2.2:4.0 |
| SWNT-3 | 1295 | 1.0:2.0:4.0 |
| SWNT-4 | 1290 | 1.0:1.4:3.7 |
| SWNT-5 | 1291 | 1.0:1.4:3.7 |
| SWNT-6 | 1292 | 1.0:1.5:3.5 |
| SWNT-7 | 1293 | 1.0:1.3:3.8 |
| SWNT-8 | 1292 | 1.0:0.7:3.0 |
| SWNT-9 | 1293 | 1.0:0.8:2.5 |
| SWNT-11 | 1292 | 1.0:0.8:2.9 |
| SWNT-12 | 1291 | 1.0:1.0:3.4 |

$^a\omega_r$ = radial breathing mode, $\omega_d$ = disorder mode, $\omega_t$ = tangential mode.
$^b\omega_r$ intensity taken at 265 cm$^{-1}$; other intensities taken at maxima.

Figure 6:
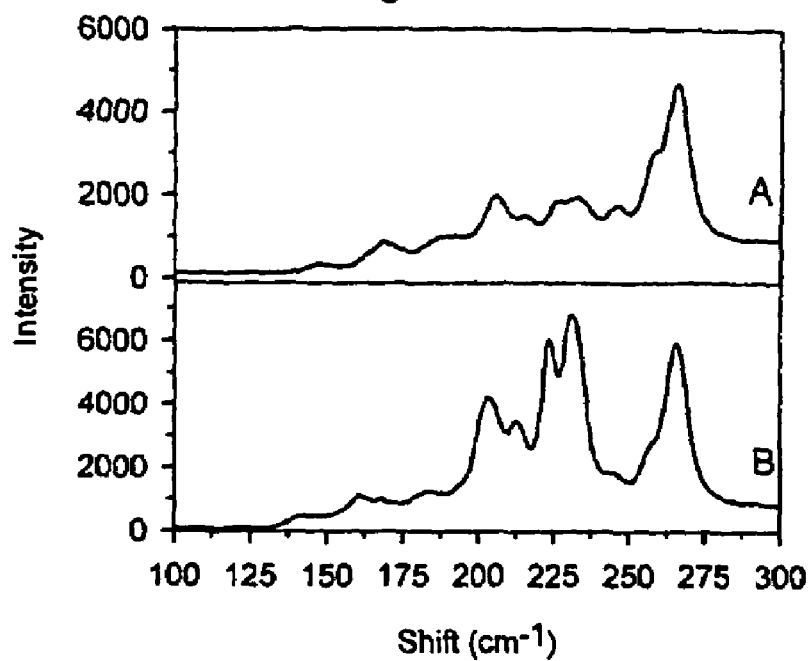
FIG. 6 shows the Raman spectra in the radial breathing mode region for (A) SWNT-4 and (B) SWNT-p.

While there is no significant change in the frequency of the disorder mode, the intensity of this mode increased relative to the intensity of the other two modes in all cases. The intensity of the tangential mode is also increased relative to the radial breathing mode in most cases, and the overall intensity is lower. In some cases, Raman spectra collected after functionalization revealed changes in the relative intensities of the peaks within the radial breathing mode region. For example, the Raman spectra in this region is shown in FIG. 6 for SWNT-p and SWNT-4.

Figure 7:
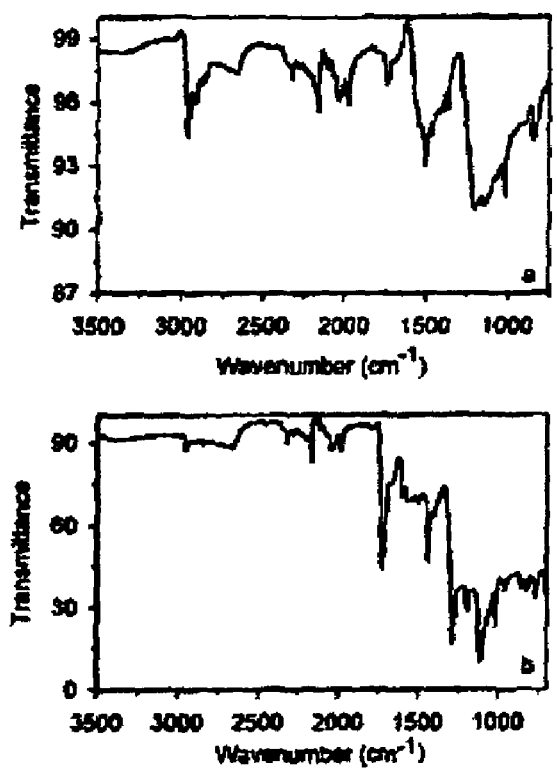
FIG. 7 shows the infrared spectra (attenuated total reflectance) of derivatized nanotubes for (A) SWNT-4 and (B) SWNT-6.

Infrared Spectroscopy. Infrared spectroscopy (FT-IR, ATR) was also used to characterize some of the derivatized materials. The spectrum of SWNT-4 (FIG. 7A) clearly shows significant C—H stretching from the tert-butyl moiety at ca. 2950 cm$^{-1}$. In the spectrum of SWNT-6 (FIG. 7B), the carbonyl (CO) stretch is apparent at 1731 cm$^{-1}$ (1723 cm$^{-1}$ in precursor diazonium salt), along with minor C—H stretching modes in the 2900 cm$^{-1}$ region.

Electron Microprobe analysis. Electron microprobe analysis (EMPA) experiments revealed 2.7 atomic % chlorine for SWNT-2 (average of four points), and 3.5 atomic % fluorine for SWNT-3 (average of five points). These percentages correspond to estimated stoichiometries of CR$_{0.036}$ for SWNT-2, and CR$_{0.05}$ for SWNT-3, where C is a carbon in the nanotube framework, and R is the functionalizing moiety. Accordingly, approximately one out of every 20-30 carbons in the nanotube bears a functional moiety.

Figure 8:
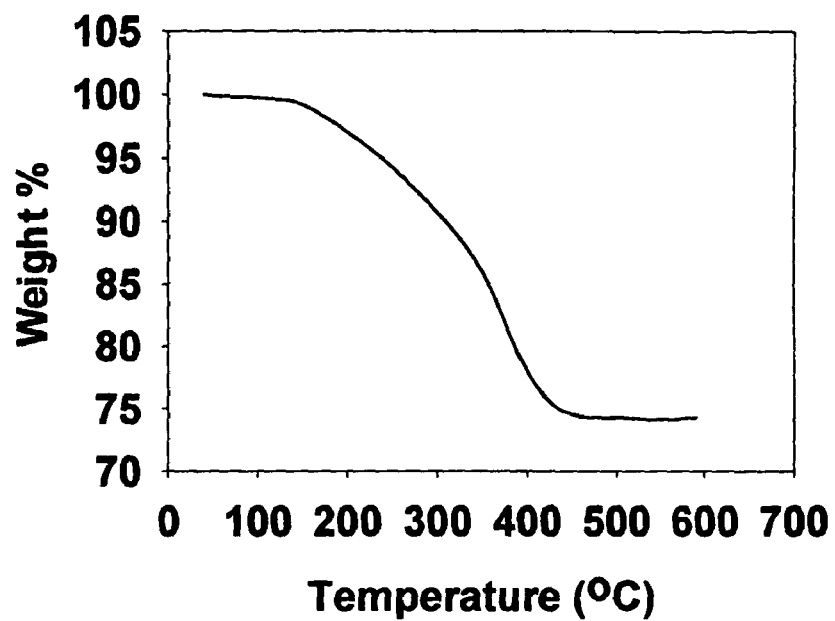
FIG. 8 shows the thermogravimetric analysis data in argon for SWNT-10.
Figure 9:
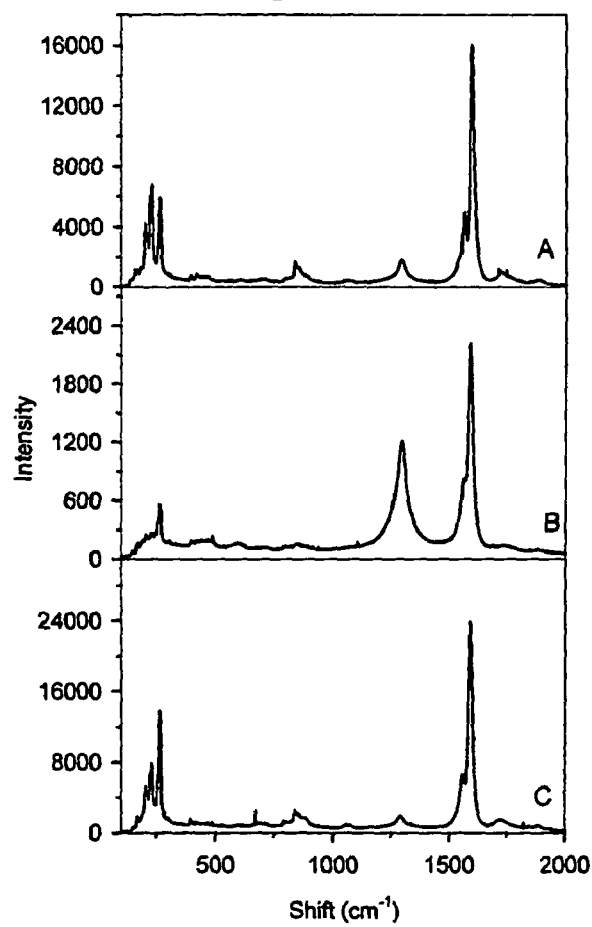
FIG. 9 shows the Raman spectra for (A) SWNT-p, (B) SWNT-2, and (C) SWNT-2 after TGA.

Thermogravimetric Analysis. In thermogravimetric analysis (TGA) of SWNT-2 (FIG. 8), a total weight loss of ca. 25%, was observed on heating to 600° C. under argon. After TGA of SWNT-2, the Raman spectrum is restored to approximately that of SWNT-p, as seen in FIG. 9. It is believed that this restoration indicates removal of the functional moieties, leaving the nanotubes intact. The stoichiometry estimated from the EMPA data predicts a weight loss of ca. 25% in the case of such a removal. Thus, these figures are in excellent agreement. The TGA and EMPA data for SWNT-3 are also in good agreement. SWNT-p suffers a ca. 5% weight loss following the same temperature profile. TGA data and estimated stoichiometries for the remaining materials (with the exception of SWNT-8, which was not performed) are shown in Table 2.

TABLE 2

Disorder mode frequency and intensity ratios

| Compound | Observed % weight loss | Stochiometry Ratio$^a$ |
|---|---|---|
| SWNT-p | 5 | NA |
| SWNT-1 | 35 | 1/25 |
| SWNT-2 | 30 | 1/27 |
| SWNT-3 | 26 | 1/20 |
| SWNT-4 | 27 | 1/34 |
| SWNT-5 | 26 | 1/31 |
| SWNT-6 | 31 | 1/28 |
| SWNT-7 | 39 | 1/36 |
| SWNT-8 | — | — |
| SWNT-9 | 36 | 1/40 |
| SWNT-11 | 28 | 1/44 |
| SWNT-12 | 24 | 1/32 |

$^a$Nanotube carbons bearing a functionalized phenyl moiety. These values are compensated for weight loss at low temperatures due to solvent evaporation and degassing (ca. 2–4% in all cases).

Table 2 reflects that the degree of functionality for these compounds is at least about one moiety to fortoy carbon atoms, and typically at least about one moiety to thirty carbon atoms. The estimated degree of functionality is ca. out of every 20 to 30 carbons in the nanotube bearing a functionality moiety.

Figure 10:
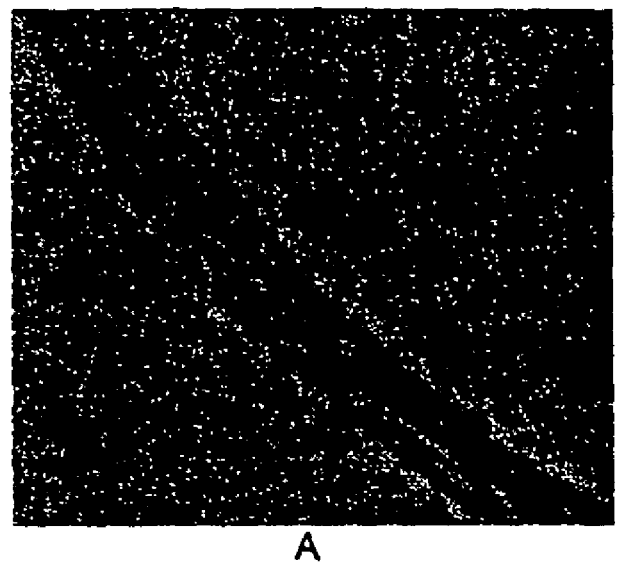
FIG. 10 shows the high-resolution TEM images for (A) SWNT-p and (B) SWNT-4. The scale bar applies to both images.
Figure 10:
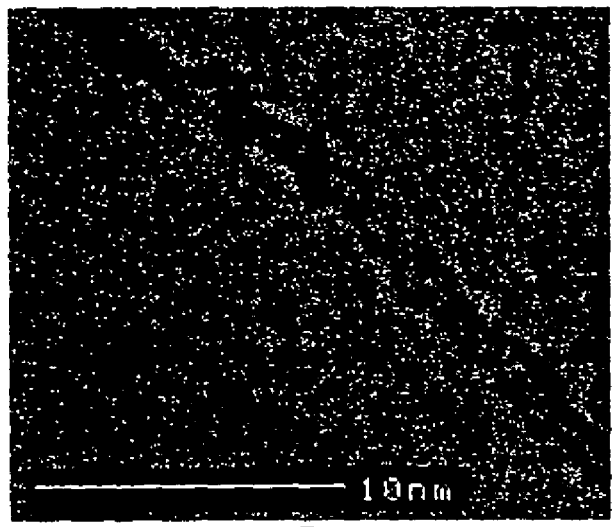

Scanning and Transmission Electron Microscopy. Due to insufficient resolution, analysis of the reaction products by scanning electron microscopy (SEM) did not reveal any visible evidence of functionalization or significant change from SWNT-p. Transmission electron microscopy (TEM) imaging of SWNT-4 revealed significant changes due to the functionalization. In images of SWNT-p (FIG. 10A), the nanotube walls are essentially clean and uniform, and there is no overcoating of graphitic carbon. Images of SWNT-4 (FIG. 10B) revealed the presence of bumps on the sidewalls of the tubes, on the order of 2-6 Å in dimension. These bumps are seen on almost all individual tubes and on the exterior of ropes, though the resolution is not sufficient to determine whether they are present on the walls of tubes buried within the ropes. These features are a result of functionalization.

Solubility. The solubility of single-wall carbon nanotubes is of significant interest to persons skilled in the art of the invention. The three solvents most applicable for the underivatized small-diameter nanotubes are dimethylformamide, chloroform, and 1,2-dichlorobenzene. SWNT-4 was the only material found to offer significantly improved solubility in organic solvents. SWNT-4 was even found to be somewhat soluble in tetrahydrofuran (THF), as opposed to a complete lack of solubility for SWNT-p in that solvent. After sonication for about 30 minutes, the THF solution was found to contain approximately 50 mg L$^{-1}$ of SWNT-4, with no visible particulate. After 36 hours, some visible particulate was present, but the solvent was still almost black. This dark color was retained for at least several weeks. Solubility in dimethylformamide, chloroform, and 1,2-dichlorobenzene was also improved, with suspensions being formed much more rapidly than in the case of SWNT-p, and higher concentrations being achievable. It is believed that this improvement in solubility is probably due to the blocking effect of the bulky tert-butyl group, which could inhibit the close contact necessary for "roping" of the nanotubes.

SWNT-5 and SWNT-8 were found to be more soluble in dimethylformamide, but solubility in other solvents (tetrahydrofuran, toluene, 2-propanol, carbon disulfide) was not improved. SWNT-9 was prepared in an effort to effect improved solubility in water and other hydrogen bonding solvents. This functionalization, however, had quite the opposite result. SWNT-9 was not dispersible in water or water/ 0.2% Triton X. Considerable difficulty was encountered in suspending SWNT-9 in dimethylformamide.

Robustness. In an effort to assess the robustness of the functionalization and preclude simple intercalation or adsorption, SWNT-1 was subjected to a variety of conditions. This material was sonicated for 10 minutes at both ambient temperature and 45° C., in both chloroform and 1,2-dichlorobenzene, filtered, and re-examined spectroscopically; no discernable changes were observed. Additionally, SWNT-1 was sonicated in 1,2-dichlorobenzene for 10 minutes to disperse the tubes, then stirred at 75° C. for 3 hours. After filtration and washing, no spectroscopic changes were observed.

SWNT-3 was re-examined by EMPA after additional sonication in acetonitrile, followed by filtration and washing. The fluorine content was 3.6 atomic %, as compared to 3.5 atomic % (vide supra), and hence within experimental limits.

C. Derivatization Mechanism

Figure 11:
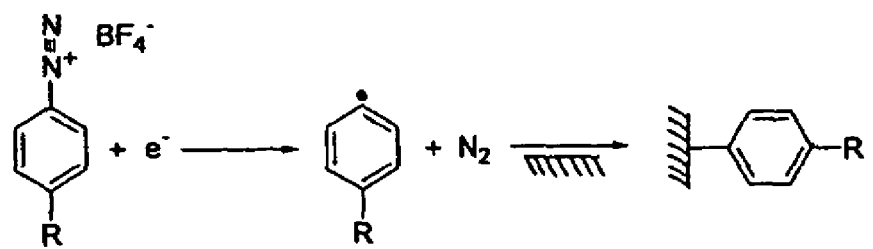
FIG. 11 shows electrochemical grafting of an aryl diazonium salt onto a carbon surface.

While not intending to be bound by theory, it is believed that the functionalization described herein is likely initiated in a manner similar to that shown in FIG. 11. The aryl radical that is presumably generated on reduction may react with a nanotube, leaving an adjacent radical that may further react or be quenched by a solvent or some impurity, or oxygen. The propensity of the initial aryl radical to dimerize or abstract a hydrogen atom from the solvent is minimized by the fact that the radical is generated at the surface of the nanotube where reaction is desired. It is noted that although the reaction may proceed through an aryl cation, the mechanism is irrelevant to the final product.

Herein lies one principle advantage of utilizing an electrochemical process, as opposed to a solution phase method in which the diazonium salt reduction is catalyzed by copper or some other metal. Since the nanotubes would be present in solution at quite low concentration, the aryl radicals would likely be quenched by some other species. Dimerization of nanotubes in the present case is also unlikely, due to lack of mobility in the solid state.

Thermal Derivatization of Carbon Nanotubes with Diazonium Species

Derivatization with aryl diazonium species is not limited to the electrochemically induced reaction. That is, both direct treatment of single-wall carbon nanotubes with aryl diazonium tetrafluoroborate salts in solution, and in-situ generation of the diazonium with an alkyl nitrite are effective means of functionalization. In-situ generation of the diazonium species has advantages in that this method can avoid the necessity of isolating and storing potentially unstable or light sensitive aryl diazonium species. The temperature utilized during the thermal reaction would be at most about 200° C., and typically at most about 60° C. In some cases, direct treatment with pre-formed diazonium salts is observed to be effective at moderate or even room temperature, and it is expected that reactions could be observed at temperatures below room temperature.

A. EXAMPLES NOS. 12-17

The nanotubes used in this investigation were again produced by a gas-phase catalytic process developed by Smalley et al., and are now commercially available (Carbon Nanotechnologies Inc., HiPco material). The production material was purified by oxidation in wet air at 250° C. for 24 hours, then stirring in concentrated hydrochloric acid at room temperature for 24 hours. The resulting material was washed with copious amounts of water, then 10% aqueous sodium bicarbonate, and finally with additional water. After drying under vacuum, the material was used for the functionalization reactions.

Figure 12:
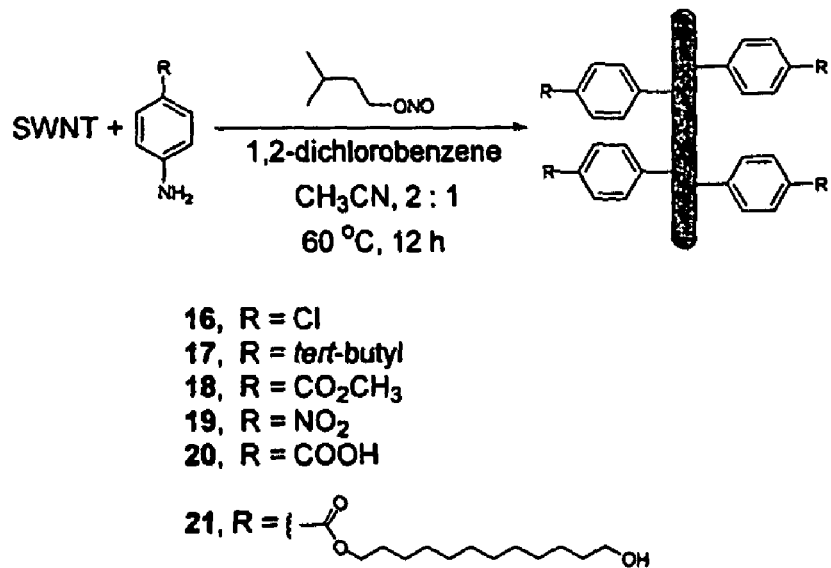
FIG. 12 shows the reaction sequence for derivatization of single-wall carbon nanotubes by in-situ generation of the diazonium species, and examples of functionalized phenyl moieties employed in reactions.

The reaction sequence is depicted in FIG. 12. In a typical experiment, ~8 mg of single-wall carbon nanotubes was sonicated for 10 minutes in 10 mL of 1,2-dichlorobenzene (ODCB). To this suspension was added a solution of the aniline derivative (2.6 mmol, ca. 4 equiv/mol of carbon) in 5 mL of acetonitrile. After transfer to a septum capped reaction tube (Ace Glass, #8648-03) and bubbling with nitrogen for 10 min, 4.0 mmol of isoamyl nitrite was quickly added. The septum was removed and replaced with a Teflon screw-cap, and the suspension was stirred at 60° C. for approximately 15 hours. Due to the system utilized, considerable pressure was attained in the vessel due to the evolved nitrogen. This was alleviated by partially unscrewing the cap for venting every ~30 min for the first 3 hours.

After cooling to ~45° C., the suspension was diluted with 30 mL of dimethylformamide (DMF), filtered over a Teflon (0.45 μM) membrane, and washed extensively with DMF. Repeated sonication in, and further washing with DMF constituted purification of the material.

B. Characterization

Figure 13:
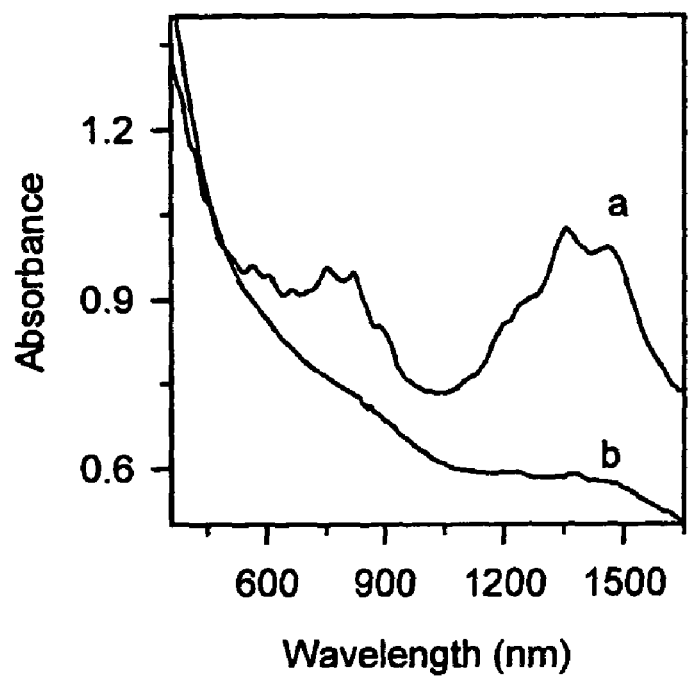
FIG. 13 shows the absorption spectra in dimethylformamide for (A) SWNT-p and (B) 18. The spectra for 16, 17, and 19 are similar, with little or no visible structure. The spectrum of the material from the sequence to produce 20 was essentially equivalent to that shown for SWNT-p.
Figure 14:
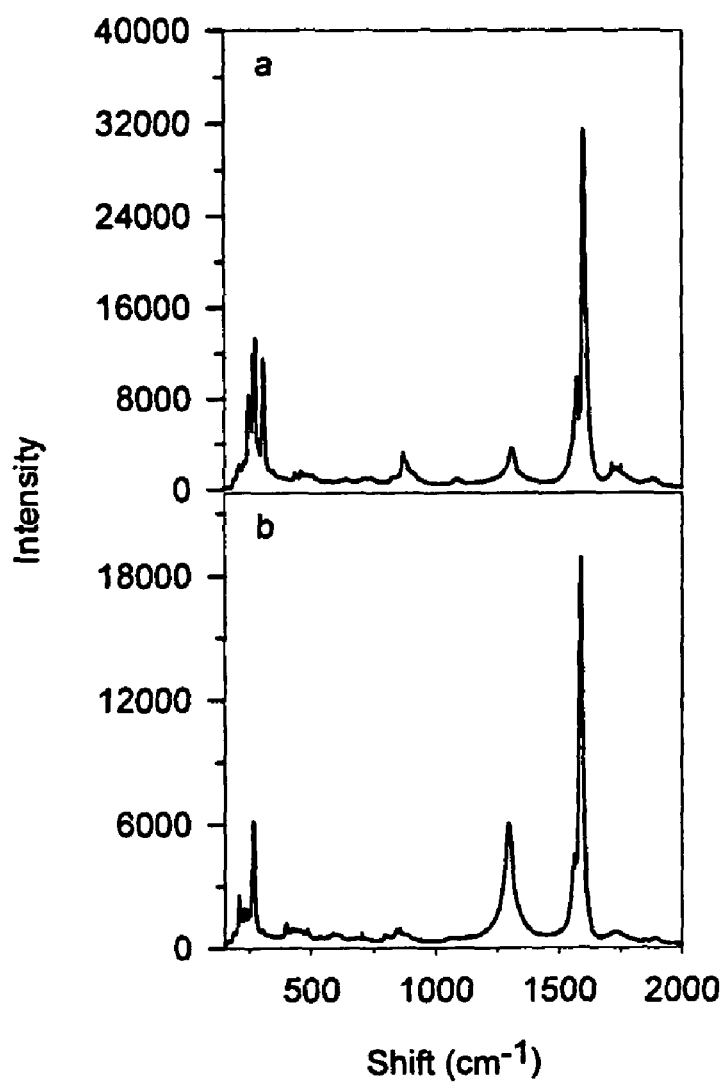
FIG. 14 shows the Raman spectra from solid samples, with excitation at 782 nm, for (A) SWNT-p and (B) 17. The Raman spectra of 16, 18, and 19 are similar, but with differing ratios of the peak intensities. In all these cases, the relative intensity of the disorder mode is increased. The spectrum of the material from the sequence to produce 20 was essentially equivalent to that shown for SWNT-p.

Functionalized nanotube materials 16-19 and 21 displayed significantly altered spectroscopic properties, akin to those reported for materials derivatized via the electrochemical method described above. For example, the UV/vis/NIR absorption spectrum of 18 (FIG. 13) shows an almost complete loss of the van Hove singularities. This loss of structure is characteristic of the disrupted π-system, and again indicates covalent modification of the nanotubes. In the Raman spectra reflected in FIG. 14, the overall intensity of the scattered light is lower, and the relative intensities of the three main modes are altered.

Relative to the tangential mode at ca. 1590 $cm^{-1}$, the intensity of the radial breathing mode (ca. 250 $cm^{-1}$) is decreased, and the intensity of the disorder mode (1290 $cm^{-1}$) is significantly increased. The increase in the relative intensity of the disorder mode can be attributed to an increased number of $sp^3$-hybridized carbons in the nanotube framework, and can be taken as a crude measure of the degree of functionalization. Additionally, as previously discussed, the functionalized phenyl moieties attached to the nanotubes can be removed by heating in an argon atmosphere, and that thermal gravimetric analysis (TGA) consequently provides a quantitative estimate of the degree of functionalization. Upon heating 16-19 to 600° C. in an argon atmosphere, the observed weight loss values were as follows, with the value previously reported for the same materials prepared via the electrochemical technique in parenthesis: 16: 26% (30%), 17: 25% (27%), 18: 26% (31%), 19: 23% (26%) 21 (not prepared by the electrochemical technique). Material 20 did not display similar changes in the spectroscopic properties or significant mass loss in TGA, even though this moiety can be successfully attached by the electrochemical technique. The ester bearing material 18 was successfully prepared, in principle giving access to the carboxylic acid moiety via hydrolysis.

It is of primary interest to compare the degree of functionalization achievable by the thermal process to that obtained by the electrochemical processes of the present invention. Experiment Nos. 13-18 were performed with a large excess of the aniline derivative, i.e. sufficient to provide the diazonium species in amounts equivalent to the amount of diazonium tetrafluoroborate salts used in the previously discussed reported electrochemical examples. Hence, these Examples Nos. 13-18 are comparable in this fashion.

For material 16, straightforward comparison is available through electron microprobe analysis. This analysis gave a value of 2.2 atomic % chlorine, relative to 97 atomic % carbon. Similar material prepared by the electrochemical technique was analyzed to have 2.7 atomic % chlorine, relative to 96 atomic % carbon (vide supra).

The TGA data also give additional insight into the relative efficiency of the thermal method. For example, the mass loss for 19 corresponds to an estimated 1 in 37 carbons in the nanotubes being functionalized, versus the 1 in 34 ratio achieved by the electrochemical method. It is believed that the thermal technique is then comparable in its effectiveness to the electrochemical method for the equivalent material (SWNT-5). It is believed that optimization of the conditions could provide a higher degree of functionalization. The observed efficacy is sufficient to significantly alter the properties of the single-wall carbon nanotubes, and will likely be satisfactory for numerous applications, such as cross-linked materials and composite formation as discussed below.

The thermal reaction of the present invention was found to be nearly as efficacious as the electrochemical process of the present invention, although, in certain respects, this thermal reaction is simpler to execute and more adaptable for scalability.

It is again noted that the chemical derivatization of nanotubes can also be successfully performed using pre-formed diazonium species. The diazonium species can be prepared beforehand, isolated, and added to the mixture. The derivatization can then be induced thermally. Additional variations include variations in the temperature of the process (ambient temperature and higher and lower temperatures), ratio of reactants, and a variety of organic solvents.

Photochemical Derivatization of Carbon Nanotubes with Diazonium Species

EXAMPLE NO. 18

Figure 15:
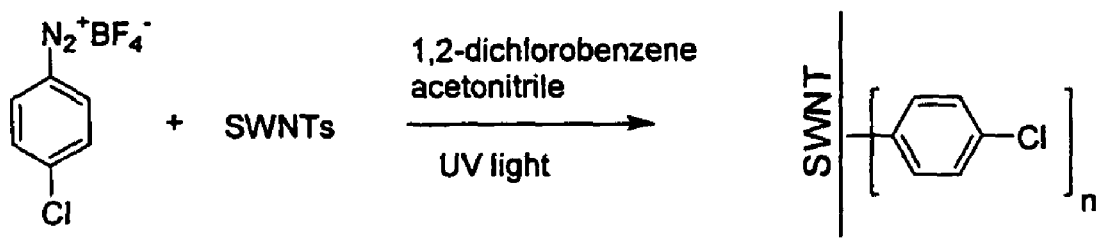
FIG. 15 shows the reaction sequence for photochemical derivatization of a single-wall carbon nanotube.

Derivatization with aryl diazonium species can also be induced photochemically. A photochemical reaction was performed utilizing 4-chlorobenzenediazonium tetrafluoroborate, which is the same diazonium species prepared and utilized in Example No. 2. Thus, a suspension of SWNT-p in 1,2-dichlorobenzene was created by sonication. To this suspension was added a portion of the diazonium salt dissolved in minimal acetonitrile. The resulting mixture was stirred while residing within the chamber of a photochemical reaction apparatus, with an excitation wavelength of ca. 254 nm (an ultraviolet light source). The light source for the photochemically induced reaction may be any wavelength, and typically is an ultraviolet or visable wavelength. This reaction is reflected in FIG. 15. The resultant material was similar in all respects to SWNT-2 that was prepared by the electrochemical technique of the present invention.

This experiment further confirmed that reaction of the diazonium salt leads to covalent attachment to the nanotube.

Controlled, Site-Specific Functionalization of Carbon Nanotubes with Diazonium Species By utilizing the electrochemically induced reaction of the present invention, control can be exerted to derivatize the nanotubes at specific sites. Existing technologies (M. S. Fuhrer, et al., "Crossed Nanotube Junctions" Science, 288, 21 Apr. 2000, page 494; Yu Huang, et al., "Directed Assembly of One-Dimensional Nanostructures into Functional Networks" Science, 291, 26 Jan. 2001, page 630; Yi Cui, et al. "Functional Nanoscale Electronics Devices Assembled Using Silicon Nanowire Building Blocks" Science, 291, 2 Feb. 2001, p 851) can be used to prepare a crossbar architecture of nanotubes, wherein one nanotube is fixed to a substrate and a second nanotube is suspended a finite distance above. Both nanotubes can be individually addressed electrically. Application of opposite potentials to the two tubes causes the top tube to deform and essentially come into contact with the lower tube. "Contact" as used herein means both actual physical contact, but also proximity of the entities within an infinitesimally small distance (referred to as van der Walls contact), in which the entities may influence each other on a molecular and electronic scale.

This deformation results in two features of significance. First, the top tube is physically deformed, leading to a potentially higher chemical reactivity at the point of deformation, based on current understanding of the effects of curvature strain on reactivity. This feature would allow selective functionalization at the junction via the electrochemical technique of reaction with diazonium salts. Secondly, higher potential is achieved at the point of "cross" between the tubes.

In the present invention, directed functionalization of the crossed-nanotube junctions can be performed by applying a potential to the ends of the nanotubes (as is known in the art) in the presence of $\alpha,\omega$-bis(diazonium) salts or mono-diazonium salts with an interacting group at the opposite end would permit functionalization at the cross point domain.

Any cross bar array of nanotubes could be functionalized by such processes. For instance, a crossbar architecture of nanotubes will be prepared by fluid flow over a patterned substrate, or by direct tube growth between posts, or by some other method. Furthermore, the diazonium salt assembly described here could occur in a diazonium solution, with voltages on orthogonal tubes, regardless of the assembly method for the tube arrays. Application of potentials to the nanotubes in the presence of diazonium salts would permit functionalization at the cross point domain.

The diazonium species are directed by the potential existing at the junction to react with the surface of the nanotube, thus placing functional molecular devices at the junctions. Site-specific functionalization could enable the use of nanotubes in molecular electronic applications since device functionality is critical at the cross points. The crossed nanotubes therefore provide a method of directly addressing the functionalized molecules, including molecules that function as molecular switches, molecular wires, and in other capacities and uses as is generally known in the art.

Furthermore, this process would allow for attachment of different molecules to nanotube cross points, i.e., controlled attachment of two or more different chemical functionalities to different locations on nanotubes. This would be performed by applying a potential at a specified set of positions while in a solution of a first diazonium salt, then moving to a solution of a second diazonium salt and applying a potential at other positions, etc. In addition, site specific functionalization will allow individual molecules or groups of molecules to be electrically addressed by metallic contact pads or other contact means as are known in the art. Just such a molecule of electronic interest is incorporated into SWNT-8.

Application of Chemically Modified Carbon Nanotubes in Polymer Composite Materials Polymer and polymer/composite materials are widely used for structural materials and a variety of other applications. The derivatized carbon nanotubes made using the processes disclosed herein can be used in combination with existing polymer matrices to create new polymer/composite materials. In general, possible composite materials could be made with chemically modified nanotubes and thermoplastics, thermosets, elastomers, and others. There are a multitude of variations in the chemical structure of the polymer matrix, i.e. polyethylene, various epoxy resins, polypropylene, polycarbonate etc. There is also a host of variations possible in the chemical groups that can be attached to the nanotubes. According, it is possible to select a specific polymer and specific moiety to enhance the properties of the particular polymer/composite material desired.

Thus, the polymer/composite material will have significantly enhanced properties, such as, for example, enhanced strength and/or conductivity. And, when modified with suitable chemical groups, the nanotubes will be chemically compatible with the polymer matrix, allowing transfer of the properties of the nanotubes (especially mechanical strength) to the properties of the composite material as a whole. Typically, to achieve this, the modified carbon nanotubes can be thoroughly mixed (physically blended) with the polymeric material, and allowed to react at ambient or elevated temperature.

Figure 16:
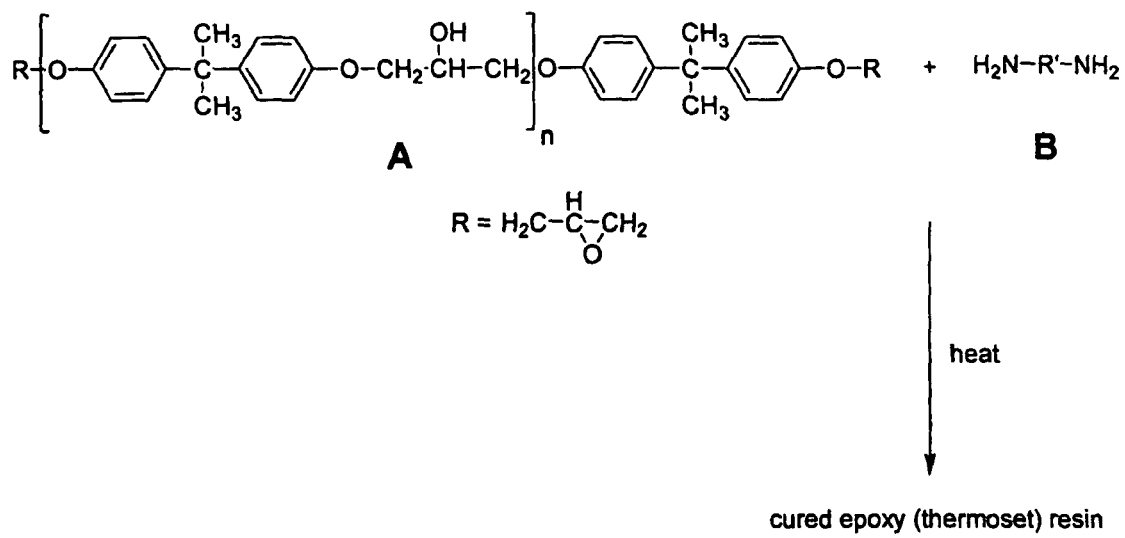
FIG. 16 shows an example of the portions comprising an epoxy resin.

Thermosets. It may be desired to form a polymer/composite material in which the carbon nanotubes are chemically bound at multiple points to the polymer (thermosets). For example, this can be done, for example, utilizing an epoxy resin. Epoxy resins are typically composed of two portions that are mixed in a certain ratio. The resulting mixture then hardens, or "cures," over a period of time into an adhesive or structural material. The two parts are the epoxy portion (labeled "A" in FIG. 16, in this case derived from the reaction of bisphenol-A with epichlorohydrin) and the curing agent (labeled "B" in FIG. 16). The curing agent contains chemical groups that react with a repeatedly occurring chemical group in the epoxy portion. I.e., the cured or cross-linked resin results from the reaction of A (specifically, the terminal epoxide functionalities) with B (specifically, the terminal amine functionalities). Because both the epoxy portion and the curing agent contain numerous reactive groups, a "cross-linked" material is created, with numerous chemical bonds that impart strength to the cured material (labeled "C" in FIG. 16). The result of the reaction is a highly cross-linked thermoset material.

Figure 17:
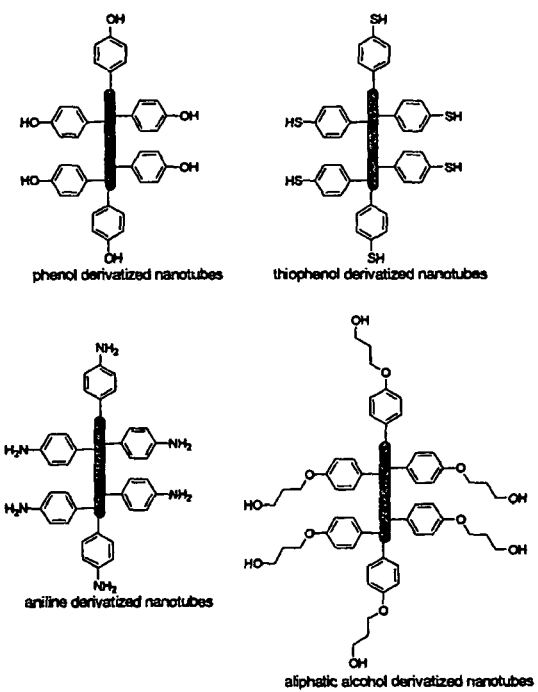
FIG. 17 shows examples of nanotubes that are chemically modified with groups compatible with the curing agent portion, and reactive with the epoxy portion of a thermosetting resin.

A wide variety of commercially available epoxy components exist, where the chemical structure of both parts A and B can vary greatly. For example, curing agents may be based on diamines, polymercaptans, phenol containing materials, etc., and may be polymeric. The addition of chemically modified carbon nanotubes to this type of system will greatly increase the strength of the resulting material, due to the strength of the nanotubes themselves. The nanotubes can be chemically modified with groups that are compatible with either the epoxy portion or the curing agent portion. For example, modified nanotubes can be prepared as shown in FIG. 17. (In the figures, the shaded cylinder represents the carbon nanotubes).

Figure 18:
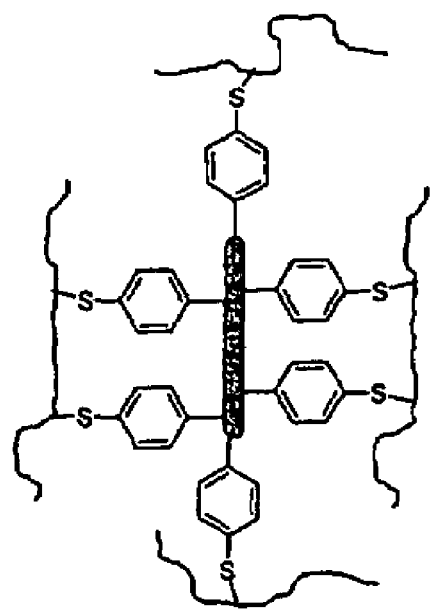
FIG. 18 shows a schematic depiction of carbon nanotube containing composite material where the freehand lines represent the polymer matrix that is cross-linked by the chemically modified carbon nanotubes, creating a thermosetting composite material.

Carbon nanotubes thus modified will be thoroughly mixed with either the curing agent portion or the epoxy portion. The resulting material will then be thoroughly mixed with the second portion and allowed to react, or cure at either ambient or elevated temperature, depending on the particular system. The resulting composite material will then be cross-linked not only by the curing agent, but also by the modified carbon nanotubes, via, for example, aryl-thioether linkages, as shown in FIG. 18, where the freehand lines schematically represent the polymer matrix.

These types of materials can be prepared using a variety of modified carbon nanotubes, exemplified by the examples in FIG. 17. Thus, the linkages between the polymer matrix and the nanotubes could be ether, thioether, amine, salt bridge (such as SWNT-11 in an amine containing host polymer) or other linkages. It is understood that the direct chemical bond between the nanotubes and the surrounding polymer matrix will enable the transference of the strength properties of the nanotubes to the composite material itself. It is also noted that enhancement of the material properties by the nanotubes may be caused by factors other than such direct chemical bonding; for example, improved dispersion of the nanotubes within the polymer matrix, enabled by the functionalization, may allow enhancement.

Figure 19:
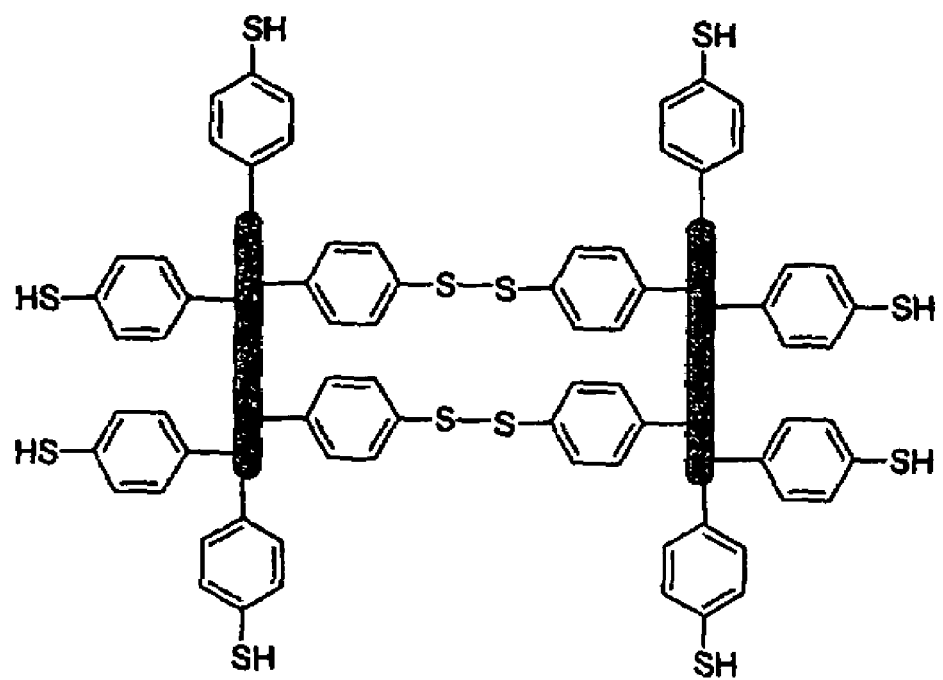
FIG. 19 shows a depiction of chemically modified carbon nanotubes cross-linked via disulfide linkages.

In addition to the chemical bond between the nanotubes and the surrounding polymer matrix, in the case of thiophenol derivatized nanotubes, there will be a chemical interaction between the nanotubes themselves. The formation of disulfide linkages between nanotubes, as shown in FIG. 19, will serve to further strengthen the material. The disulfide linkages can be further reduced (chemically, for instance) to once again provide the non-crosslinked tubes. Hence, this is a stealth-like crosslinking. In fact, such cross-linked nanotubes will represent an enhanced strength material in their own right for some applications.

Figure 21:
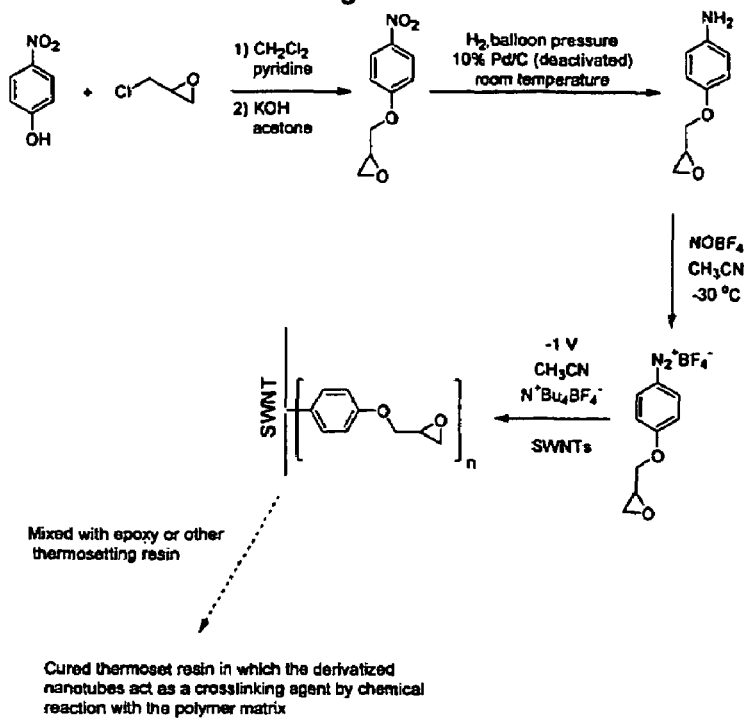
FIG. 21 shows the preparation of carbon nanotubes chemically modified with pendant epoxy groups that are compatible with the epoxy portion of a resin and reactive with the curing agent portion of a thermosetting resin, as reflected in FIG. 16.

Another possibility is modification of carbon nanotubes with chemical groups that are compatible with the epoxy portion rather than the curing agent portion, such as, for example, shown in FIG. 21. The material resulting from the incorporation of nanotubes derivatized in this manner would again be a chemically bound, three-dimensional network, cross-linked by both the curing agent and the chemically modified nanotubes.

Figure 22:
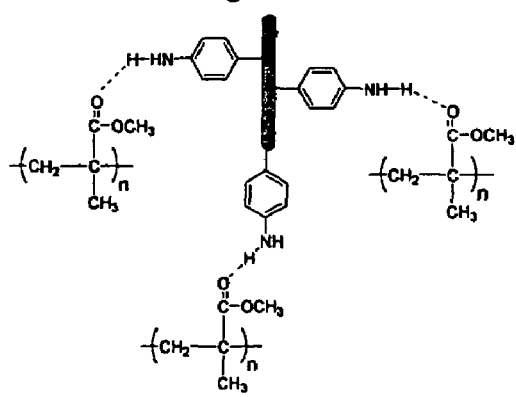
FIG. 22 shows an example of a composite material based on poly(methylmethacrylate) and chemically modified carbon nanotubes, based on a hydrogen bonding motif (indicated by the dashed lines).

Other specific chemical interactions between modified carbon nanotubes and a polymer matrix are also possible. For example, a system based on a hydrogen bonding interaction is shown in FIG. 22. This type of interaction would be in an extended three-dimensional network, again imparting the strength of the nanotubes to the composite material.

Figure 20:
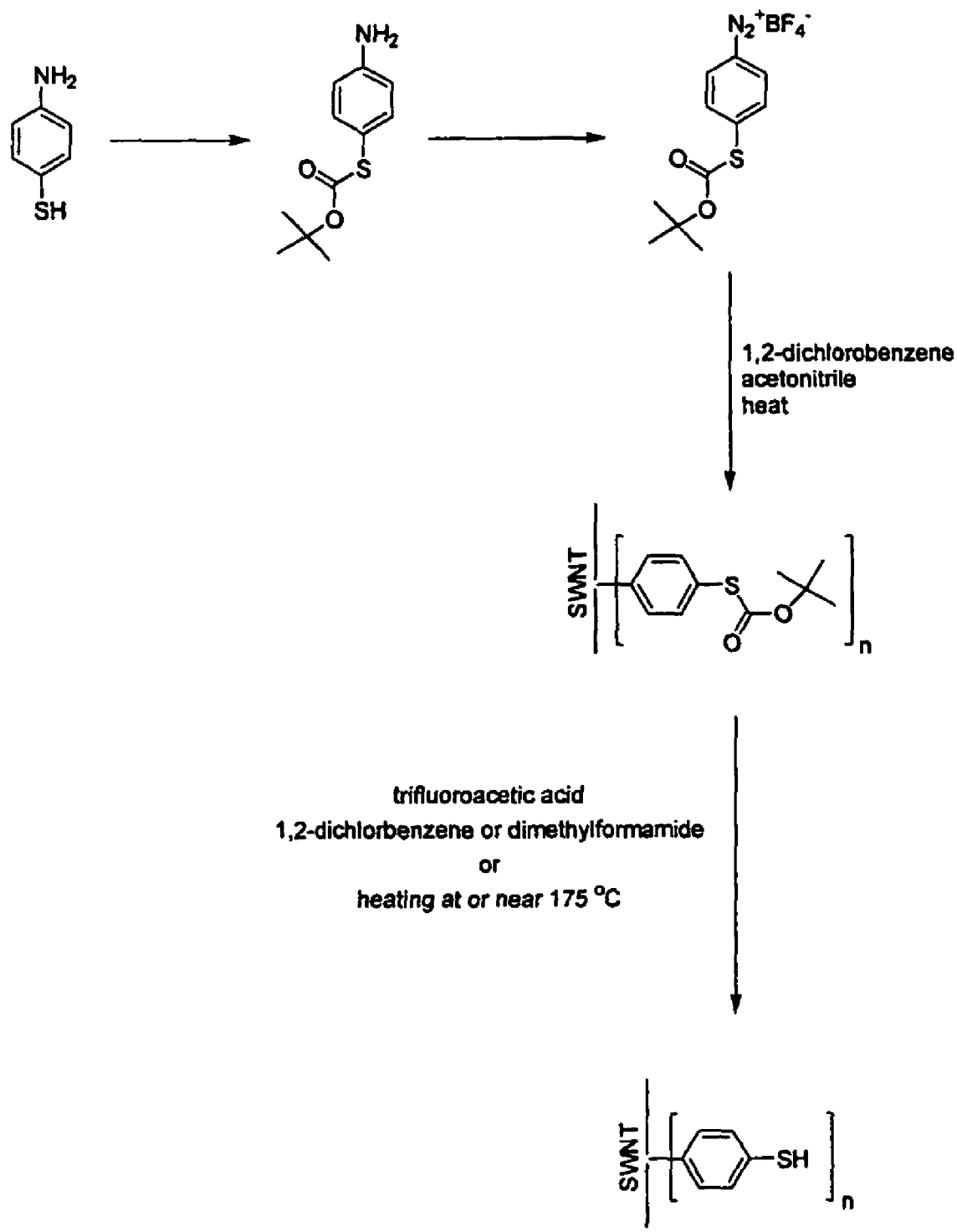
FIG. 20 shows the preparation of nanotubes chemically modified with thiophenol moieties.

Utilizing the electrochemical process described in this invention, the derivatized nanotubes reflected in FIG. 20 were prepared. From this, what is believed to be a step of deprotection of the thiol was performed by treatment with trifluoroacetic acid in 1,2-dichlorobenzene (acid hydrolysis). Alternatively, this step could be performed by treatment with trifluoroacetic acid in dimethylformamide, or by thermolysis at or about 175° C. Again, the functionalized nanotubes formed as reflected in FIG. 20 would chemically react with, for example an epoxy resin, with the free thiol group (SH) acting as a crosslinking agent.

Thermoplastics. In addition to thermosets, derivatized nanotubes can be utilized for thermoplastics. As in the case of thermosets, the derivatized nanotubes may or may not be chemically bound to the polymer matrix. It is understood that a modest degree of chemical attachment between the derivatized nanotubes and the polymer matrix could be tolerated, while retaining the thermoplastic properties (specifically, the ability to heat and reform the material without significant degradation). As noted above, physical blending of the carbon nanotubes with the polymer can be enhanced by the derivatization process (specifically by making the nanotubes more compatible with, or more soluble in, the host polymer).

For instance, a polymer/composite material containing pure (and underivatized) single-wall carbon nanotubes may be desired so that the polymer would have certain enhanced conductive properties; however, the pure and underivatized carbon nanotubes may not sufficiently disperse in the polymer. By derivatizing the nanotubes with a particular moiety, the derivatized nanotubes could then be dispersed adequately.

Because the derivatization of the nanotube may likely have affected the conductivity of the nanotube (and will thus effect the conductivity of the polymer/composite), it may be desirable to reverse the derivatization process to remove the functional groups from the nanotubes after dispersal. In this manner, the conductivity of the material can be recovered. This can be done by any process that reverses the derivatization, such as raising the temperature of the polymer/composite material to a temperature at which the functional group disassociates. Typically, this temperature appears to be at least about 250° C.

A. EXAMPLE NOS. 19-25

Moreover, the thermoplastic may also be formed utilizing the derivatized carbon nanotube. The functional groups, while not necessarily chemically bond to the polymer, would be physical extensions from the tube (like branches from a tree) that will afford additional strength to the polymer/composite materials. This enhancement may be due to a roughening effect on the nanotube surface, increasing friction and reducing sliding of the polymer matrix along the nanotube length. As is understood in the art, such as an effect would further enable transference of the desirable nanotube properties to the composite material.

Utilizing processes discussed above the following functionalized single-wall carbon nanotubes where prepared where n=1 in 20 to 1 in 40 functional groups per nanotube carbons):

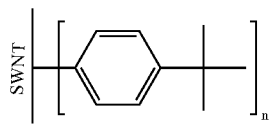

17

This derivatized material (17) was dispersed in High-Impact-Polystyrene (HIPS) at various concentrations. Tensile strength, tensile modulus, and % strain to failure data of the resulting composite material were then gathered. The results of these examples are reflected in Table 3.

TABLE 3

| Material | Tensile Strength (MPa) | Tensile Modulus (MPa) | % Strain to Failure |
|---|---|---|---|
| HIPS (pure) | 18.1 | 454.5 | 56.4 |
| 1 wt % 17 | 32.5 | 729.3 | 4.6 |
| 3 wt % 17 | 17.8 | 821.3 | 2.2 |
| 3 wt % pristine* | 22.8 | 560.0 | 11.0 |
| 5 wt % 17 | 26.3 | 736.5 | 3.9 |
| 7 wt % 17 | 22.0 | 724.4 | 3.1 |

*3 wt. %, unfunctionalized nanotubes (SWNT-p), for direct comparison

On the whole, there is a substantial improvement in the tensile properties of the polymer/composite materials with the functionalized nanotubes. There is improvement over both the pristine HIPS polymer, and over the composite of HIPS and unfunctionalized nanotubes.

Figure 23:
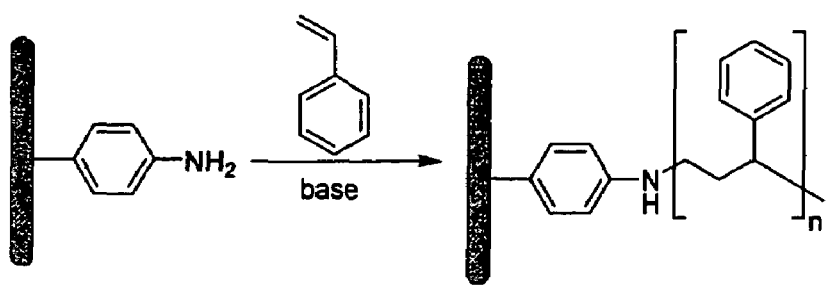
FIG. 23 shows an example of chemically modified nanotubes being used in a polymerization process to grow the polymer from the nanotubes.

Polymerization. Furthermore, a polymer that includes carbon nanotubes can be formed by derivatizing the carbon nanotubes with a functional group that is capable of polymerizing or initiating a polymerization. Once the functional group is attached, standard polymerization techniques can then be employed to grow the polymer from the functional group in situ. I.e., the functional group attached to the nanotube could be used as a generator of polymer growth. Such standard polymerization techniques could be any of the standard known types, such as radical, cationic, anionic, condensation, ring-opening, methathesis, or ring-opening-metathesis (ROMP) polymerizations, when appropriate groups are bound to the nanotubes. For instance, FIG. 23 reflects an example of a carbon nanotube that has been derivatized with a functional group 4-aminophenyl that is subsequently polymerized with styrene to grow the polymer from the functional group. Accordingly, the functional group attached to the nanotube would be a chemically active part of the polymerization, which would result in a composite material in which the nanotubes are chemically involved.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A product made by the process comprising:
   (a) selecting a plurality of carbon nanotubes; and
   (b) reacting the plurality of carbon nanotubes with an aryl diazonium specie to form carbon nanotubes derivatized with an aryl moiety, wherein reacting comprises bonding said aryl moiety to the carbon nanotube surface carbon atoms, wherein there is at least about one aryl moiety to forty carbon atoms on the carbon nanotube surface.

2. The product of claim 1 further comprising dispersing the derivatized carbon nanotubes in a solvent.

3. A product made by the process comprising:
   (a) selecting an assembly of single-wall carbon nanotubes;
   (b) immersing the assembly in a solution comprising an aryl diazonium specie; and
   (c) applying a potential to the assembly to electrochemically react the assembly with the aryl diazonium specie, wherein electrochemically reacting comprises bonding an aryl moiety to the carbon nanotube surface carbon atoms, wherein there is at least about one aryl moiety to forty carbon atoms on the carbon nanotube surface.

4. The product of claim 1 further comprising pre-forming the aryl diazonium specie.

5. The product of claim 1 further comprising:
   (c) mixing a precursor of the aryl diazonium specie wit the plurality of carbon nanotubes; and
   (d) generating the aryl diazonium specie, wherein the plurality of carbon nanotubes comprise a plurality of single-wall carbon nanotubes.

6. The product of claim 1, wherein the plurality of carbon nanotubes comprise single-wall carbon nanotubes.

7. The product of claim 6, wherein the single-wall carbon nanotubes have an average diameter of at most about 0.7 nm.

8. The product of claim 1, wherein the plurality of carbon nanotubes are electrochemically reacted with the aryl diazonium specie.

9. The product of claim 1, wherein the plurality of carbon nanotubes are thermally reacted with the aryl diazonium specie.

10. The product of claim 1, wherein the aryl diazonium specie is generated in situ.

11. The product of claim 1, wherein the aryl diazonium specie is preformed before the plurality of carbon nanotubes are thermally reacted with the aryl diazonium specie.

12. The product of claim 1, wherein the plurality of carbon nanotubes are photochemically reacted with the aryl diazonium specie.

13. The product of claim 1, wherein the plurality of carbon nanotubes is an assembly of carbon nanotubes.

14. The product of claim 13, wherein the assembly is selected from the group consisting of a bucky paper and a mat.

15. The product of claim 13 further made by the process comprising:
   (a) immersing the assembly in a solution comprising the aryl diazonium specie; and
   (b) applying a potential to the assembly.

16. The product of claim 15, wherein the potential is a negative potential.

17. The product of claim 15, wherein the solution further comprises a supporting electrolyte specie.

18. The product of claim 15, wherein the step of applying a potential to the assembly comprises holding the assembly with an alligator clip treated with a colloidal silver paste.

19. The product of claim 1, further made by the process comprising sonicating the derivatized carbon nanotubes.

20. The product of claim 1 or 3, wherein there is at least about one aryl moiety to thirty carbon atoms on the carbon nanotube surface.

21. The product of claim 1, wherein the reaction is a thermal reaction at a temperature of at most about 200° C.

22. The product of claim 1, wherein the reaction is a thermal reaction at a temperature of at most about 60° C.

23. The product of claim 1 further comprising photochemically treating the mixture of the plurality of carbon nanotubes and the aryl diazonium specie.

24. The product of claim 23, wherein the photochemical treatment comprises the use of an ultraviolet light source.

25. The product of claim 23, wherein the photochemical treatment comprises the use of a visible light source.

26. The product of claim 5, wherein the precursor of the aryl diazonium specie is an aniline derivative and the aryl diazonium specie is generated with a nitrite.

27. A solution of single-wall carbon nanotubes made by the process comprising:
   (a) providing a plurality of derivatized single-wall carbon nanotubes, wherein:
      (i) an aryl diazonium specie derivatized the plurality of single-wall carbon nanotubes with an aryl moiety bonded to the carbon nanotube surface carbon atoms; and
      (ii) there is at least about one aryl moiety to forty carbon atoms on the carbon nanotube surface; and
   (b) mixing the plurality of derivatized single-wall carbon nanotubes in a solvent, wherein the derivatized plurality of carbon nanotubes are dispersed in the solvent.

28. A product made by the process comprising:
   (a) preparing an assembly, wherein
      (i) the assembly comprises a first plurality of carbon nanotubes and a second plurality of carbon nanotubes; and
      (ii) wherein the carbon nanotubes in the first plurality and the carbon nanotubes in the second plurality can be individually addressed electronically;
   (b) immersing the assembly in an aryl diazonium specie;
   (c) applying a negative potential to the assembly to cause the first plurality to essentially come in contact with the second plurality; and
   (d) electrochemically reacting the assembly with the aryl diazonium specie, wherein electrochemically reacting comprises bonding an aryl moiety to the surface of the carbon nanotubes comprising the assembly at the cross points of the first plurality and the second plurality.

29. A product made by the process comprising:
   (a) preparing an assembly of carbon nanotubes, wherein
      (i) the assembly comprises a first plurality of carbon nanotubes and a second plurality of carbon nanotubes; and
      (ii) wherein the carbon nanotubes in the first plurality and the carbon nanotubes in the second plurality can be individually addressed electronically;
   (b) immersing the assembly in a first aryl diazonium specie;
   (c) applying a potential to the assembly in a first direction to cause the first plurality to essentially come in contact with the second plurality;
   (d) electrochemically reacting the assembly with the first aryl diazonium specie, wherein electrochemically reacting comprises bonding a first aryl moiety to the surface of the carbon nanotubes comprising the assembly at the cross points of the first plurality and the second plurality;
   (e) immersing the assembly in a second aryl diazonium specie;
   (f) applying a potential to the assembly in a second direction to cause the second plurality to essentially come in contact with the first plurality; and
   (g) electrochemically reacting the assembly with the second aryl diazonium specie, wherein electrochemically reacting comprises bonding a second aryl moiety to the surface of the carbon nanotubes comprising the assembly at the cross points of the first plurality and the second plurality.

30. The product of claim 2, wherein the carbon nanotubes of the first plurality comprise single-wall carbon nanotubes and the carbon nanotubes of the second plurality comprise single-wall carbon nanotubes.

31. The product of claim 2, wherein the assembly is a crossbar architecture of carbon nanotubes.

32. The product of claim 2, wherein the preparation of the assembly comprises fluid flow over a patterned surface.

33. The product of claim 2, wherein the preparation of the assembly comprises direct carbon nanotube growth between posts.

34. The product of claim 1, 3 or 27, wherein the product is further comprised by about 1 in 20 to about 1 in 40 of the carbon nanotube surface carbon atoms derivatized with an aryl moiety.

* * * * *